United States Patent
Bucarey Vivanco et al.

(10) Patent No.: US 11,246,839 B2
(45) Date of Patent: Feb. 15, 2022

(54) VACCINE TREATMENT AND CONTROL INFECTIOUS AGAINST VIRAL PATHOGENS UTILIZING HEPARAN SULFATE (HS) AS CELLULAR RECEPTOR

(71) Applicant: Universidad de Chile, Santiago (CL)

(72) Inventors: Sergio Antonio Bucarey Vivanco, Santiago (CL); Andronico David Neira Carrillo, Santiago (CL); Victor Manuel Neira Ramirez, Santiago (CL)

(73) Assignee: UNIVERSIDAD DE CHILE, Santiago (CL)

( * ) Notice: Subject to any disclaimer, the term of this patent is extended or adjusted under 35 U.S.C. 154(b) by 0 days.

(21) Appl. No.: 16/859,549

(22) Filed: Apr. 27, 2020

(65) Prior Publication Data

US 2021/0059951 A1 Mar. 4, 2021

Related U.S. Application Data

(63) Continuation-in-part of application No. 15/773,350, filed as application No. PCT/CL2016/050058 on Nov. 3, 2016, now abandoned.

(30) Foreign Application Priority Data

Nov. 5, 2015 (CL) .................................. 3257-2015

(51) Int. Cl.
| | | |
|---|---|---|
| *A61K 9/00* | (2006.01) | |
| *C12P 19/04* | (2006.01) | |
| *C12P 19/18* | (2006.01) | |
| *A01N 1/02* | (2006.01) | |
| *A61K 31/737* | (2006.01) | |
| *A61K 9/50* | (2006.01) | |
| *A61K 39/12* | (2006.01) | |
| *C12N 7/00* | (2006.01) | |
| *A61P 31/20* | (2006.01) | |
| *A61K 39/00* | (2006.01) | |

(52) U.S. Cl.
CPC ............ *A61K 9/5036* (2013.01); *A61K 39/12* (2013.01); *A61P 31/20* (2018.01); *C12N 7/00* (2013.01); *A61K 2039/542* (2013.01); *A61K 2039/543* (2013.01); *A61K 2039/545* (2013.01); *A61K 2039/552* (2013.01); *C12N 2750/10034* (2013.01); *C12N 2750/10071* (2013.01)

(58) Field of Classification Search
CPC .......... C08L 5/08; A61L 24/08; A61L 29/085; A61L 27/20; A61K 47/36
See application file for complete search history.

(56) References Cited

PUBLICATIONS

Meng et al., "Effects of a chemically derived homo zwitterionic polysaccharide on immune activation in mice", Acta Biochim Biophys Sin, 2009: 737-744.*

Bucarey, S. et al. "Chitosan microparticles loaded with yeast-derived PCV2 virus-like particles elicit antigen-specific cellular immune response in mice after oral administration", Virology Journal, 2014, 11(1):1-12.*

* cited by examiner

*Primary Examiner* — Barry A Chestnut
(74) *Attorney, Agent, or Firm* — Procopio, Cory, Hargreaves & Savitch LLP

(57) ABSTRACT

Vaccines of preferential administration via mucous membranes, for the control of viral diseases generated by infectious agents that use heparan sulfate (HS) as a cellular receptor consisting of an immunogenic formulation for veterinary use, comprising an antigen whose cellular receptor is heparan sulfate (HS), a vehicle for oral, intranasal or parenteral administration, wherein said vehicle corresponds to D-glucosamine and functionalized N-acetyl-D-glucosamine biopolymers, with sulfur atoms, and/or functionalized chitosan biopolymer, with sulfur atoms, and where the antigen is microencapsulated by said types of functionalized biopolymers.

10 Claims, 11 Drawing Sheets

Specification includes a Sequence Listing.

Oral administration (comercial vs sulphated)

Oral administration (comercial vs thioled)

Nasal administration (comercial vs sulphated)

Nasal administration (comercial vs thioled)

Subcutanius administration (comercial vs sulphated)

Subcutanius administration (comercial vs thioled)

FIGURE 9A FIGURE 9B
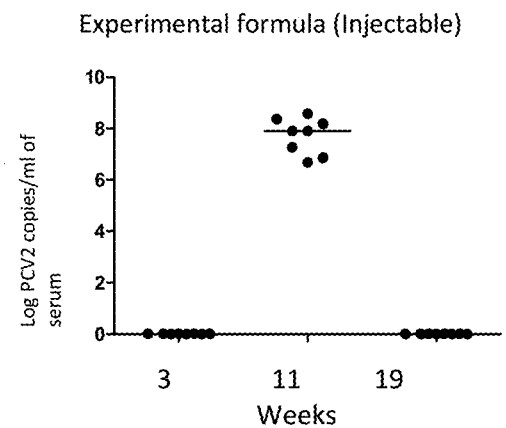
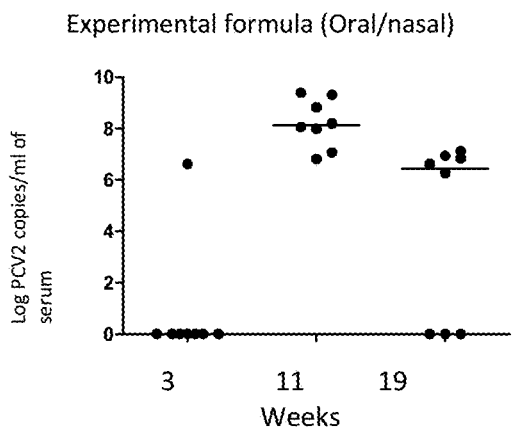
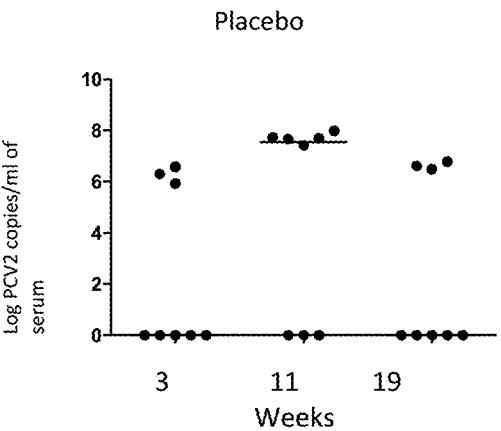
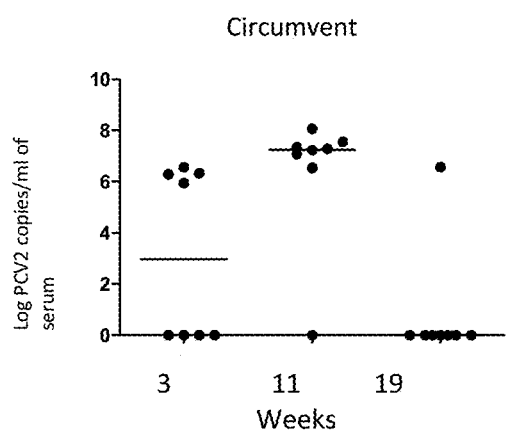
FIGURE 9C FIGURE 9D

Figure 10. Sulfated chitosan concentration effect over the PCV2 viral title

FIGURE 10

Figure 11. Sulfated chitosan molecular weight effect over the PCV2 viral title.

FIGURE 11

Figure 12. Sulfated chitosan effect over the PCV2 viral title.

FIGURE 12

SEQUENCE LISTING

<160> NUMBER OF SEQ ID NOS: 18

<210> SEQ ID NO 1
<211> LENGTH: 60
<212> TYPE: DNA
<213> ORGANISM: PCV2

<400> SEQUENCE: 1
ggatccgcca ccatggctat gacctaccca agaaggagat acagaaggag aaggcacaga        60

<210> SEQ ID NO 2
<211> LENGTH: 60
<212> TYPE: DNA
<213> ORGANISM: PCV2

<400> SEQUENCE: 2
ccaagatccc acttgggtca aattttgaga aggagacctt ggttggtgca tcctagacat        60

<210> SEQ ID NO 3
<211> LENGTH: 60
<212> TYPE: DNA
<213> ORGANISM: PCV2

<400> SEQUENCE: 3
agatacagat ggagaagaaa gaacggtatt tttaatacaa gattgagtag aacatttggt        60

```
<210> SEQ ID NO 4
<211> LENGTH: 60
<212> TYPE: DNA
<213> ORGANISM: PCV2

<400> SEQUENCE: 4
tatacaatta aaagaaccac tgttaaaact ccatcttggg ccgttgatat gatgaggttt      60

<210> SEQ ID NO 5
<211> LENGTH: 60
<212> TYPE: DNA
<213> ORGANISM: PCV2

<400> SEQUENCE: 5
aatattaacg actttcttcc tcctggtggt ggttcaaatc caagaagtgt cccatttgaa      60

<210> SEQ ID NO 6
<211> LENGTH: 60
<212> TYPE: DNA
<213> ORGANISM: PCV2

<400> SEQUENCE: 6
tactatagaa ttagaaaagt caaagttgaa ttctggcccct gctcccctat tacacaaggc     60

<210> SEQ ID NO 7
<211> LENGTH: 60
<212> TYPE: DNA
<213> ORGANISM: PCV2

<400> SEQUENCE: 7 gacagggtg ttggatcttc cgccgtaata cttgatgata acttcgtaac aaaagcaacc       60

<210> SEQ ID NO 8
<211> LENGTH: 60
<212> TYPE: DNA
<213> ORGANISM: PCV2

<400> SEQUENCE: 8
gctttgacat acgatcctta tgtcaattac agttccagac atacaataac acaacctttt     60

<210> SEQ ID NO 9
<211> LENGTH: 60
<212> TYPE: DNA
<213> ORGANISM: PCV2

<400> SEQUENCE: 9
agttatcata gtagatattt taccccaaaa cctgtgctag actctaccat cgattatttt     60

<210> SEQ ID NO 10
<211> LENGTH: 60
<212> TYPE: DNA
<213> ORGANISM: PCV2

<400> SEQUENCE: 10
caaccaaaca ataagagaaa tcaactttgg ttgaggttgc aaacagccgg taatgtggac     60

<210> SEQ ID NO 11
<211> LENGTH: 60
<212> TYPE: DNA
<213> ORGANISM: PCV2

<400> SEQUENCE: 11
catgttggcc tgggcacagc ttttgagaac tcaatctacg atcaagagta taatataaga    60
```

<210> SEQ ID NO 12
<211> LENGTH: 68
<212> TYPE: DNA
<213> ORGANISM: PCV2

<400> SEQUENCE: 12
gtcactatgt atgtacaatt cagggaattc aatcttaaag atcccccatt gaatccataa    60
gcggccgc    68

<210> SEQ ID NO 13
<211> LENGTH: 60
<212> TYPE: PRT
<213> ORGANISM: PCV2

<400> SEQUENCE: 13

Met Thr Tyr Pro Arg Arg Arg Tyr Arg Arg Arg His Arg Pro Arg
1               5                   10                  15

Ser His Leu Gly Gln Ile Leu Arg Arg Arg Pro Trp Leu Val His Pro
            20                  25                  30

Arg His Arg Tyr Arg Trp Arg Arg Lys Asn Gly Ile Phe Asn Thr Arg
35 40 45

Leu Ser Arg Thr Phe Gly Tyr Thr Ile Lys Arg Thr
50 55 60

<210> SEQ ID NO 14
<211> LENGTH: 59
<212> TYPE: PRT
<213> ORGANISM: PCV2

<400> SEQUENCE: 14

Thr Val Lys Thr Pro Ser Trp Ala Val Asp Met Met Arg Phe Asn Ile
1 5 10 15

Asn Asp Phe Leu Pro Pro Gly Gly Gly Ser Asn Pro Arg Ser Val Pro
20 25 30

Phe Glu Tyr Tyr Arg Ile Arg Lys Val Lys Val Glu Phe Trp Pro Cys
35 40 45

Ser Ile Thr Gln Gly Asp Arg Gly Val Gly Ser
50 55

<210> SEQ ID NO 15
<211> LENGTH: 60
<212> TYPE: PRT
<213> ORGANISM: PCV2

<400> SEQUENCE: 15

Ser Ala Val Ile Leu Asp Asp Asn Phe Val Thr Lys Ala Thr Ala Leu
1 5 10 15

Thr Tyr Asp Pro Tyr Val Asn Tyr Ser Ser Arg His Thr Ile Thr Gln
20 25 30

Pro Phe Ser Tyr His Ser Arg Tyr Phe Thr Pro Lys Pro Val Leu Asp
35 40 45

Ser Thr Ile Asp Tyr Phe Gln Pro Asn Asn Lys Arg
50 55 60

<210> SEQ ID NO 16
<211> LENGTH: 53
<212> TYPE: PRT
<213> ORGANISM: PCV2

<400> SEQUENCE: 16

-continued

```
Asn Gln Leu Trp Leu Arg Leu Gln Thr Ala Gly Asn Val Asp His Val
1               5                   10                  15

Gly Leu Gly Thr Ala Phe Glu Asn Ser Ile Tyr Asp Gln Glu Tyr Asn
            20                  25                  30

Ile Arg Val Thr Met Tyr Val Gln Phe Arg Glu Phe Asn Leu Lys Asp
        35                  40                  45

Pro Pro Leu Asn Pro
    50

<210> SEQ ID NO 17
<211> LENGTH: 19
<212> TYPE: DNA
<213> ORGANISM: PCV2

<400> SEQUENCE: 17
atgtccaccg cccaggagg                                                19

<210> SEQ ID NO 18
<211> LENGTH: 25
<212> TYPE: DNA
<213> ORGANISM: PCV2

<400> SEQUENCE: 18
ccgytggaga aggaaaaatg gcatc                                         25
```

VACCINE TREATMENT AND CONTROL INFECTIOUS AGAINST VIRAL PATHOGENS UTILIZING HEPARAN SULFATE (HS) AS CELLULAR RECEPTOR

FIELD OF THE INVENTION

The present invention framed in the veterinary area, is related to the development of a vaccine for the treatment and control of infectious diseases affecting the productivity of the livestock, agricultural industry and animal husbandry, more specifically, a vaccine administration via mucosal (oral or intranasal) and parenteral to control infectious diseases generated by agents such as viruses, using heparan sulfate (HS) as cell receptor.

BACKGROUND OF THE INVENTION

It is common knowledge that increased veterinary emergencies worldwide is linked to increased mobility of people, goods and animals, changes in farming systems and climate, in addition to the weakening of many health services livestock. Both in developed countries and the developing countries, sometimes no disease outbreaks have been detected by the central veterinary authorities for days or even months, which has enabled them to spread without restraint. The results have been unnecessary production losses, and outbreaks of disease outbreaks and increasing campaigns for effective disease control and eradication of the same difficulty. These trends indicate that timely warning is one of the weakest links in the systems of disease surveillance at the national, regional and international levels.

In many developing countries, systems for disease surveillance are passive and rely mostly on that report of outbreaks of disease, rather than actively monitor the situation of the same, and there is very little coordination between field veterinary services and those laboratory. Vaccines and antibiotics have been used to control infectious diseases for many years. However, antibiotics and vaccines are not always effective, often due to methods of administration. Clearly, antibiotics and vaccines cannot replace biosecurity programs, but for some diseases are needed and reduce the spread of the disease when appropriately and timely used.

It is known that in livestock, agriculture and animal husbandry industry, there are many attempts to provide vaccines to reduce disease affecting animals. Some of these vaccines are used for the control of diseases generated by infectious agents using heparan sulfate (HS) as cell receptor, where HS is a glycosaminoglycan (GAG) that can be attached to proteins forming proteoglycans (HSPG's), the which is present in all cells, both on the surface and at the level of extracellular matrix (ECM). According to the specific set of modified disaccharides HS binding sites for a variety of specific ligands are defined. In the prior art, can be found related to the role of HSPG's both infections caused by bacteria or viruses, among which may be mentioned, Garcia et al papers, J. Med Microb Diagn 2014, 3: 4. Zhu Wu and Yang et al, Biomed Environ Sci, 2011, 24 (1). 81-87. However, most of these vaccines are administered parenterally presenting several disadvantages, which are explained below. An alternative to meet the demands related to control generated by infectious agents, which has been widely explored is the development of oral vaccines for livestock, agricultural and animal husbandry industry as this administration route allows among other things diseases more effective vaccines and reduce indirect costs associated with parenteral vaccination, such as time, labor and infrastructure, induction of the inflammatory response and inclusion of foreign bodies at the site of injection as well as related stress management animal. In turn, oral vaccines, potentially mixed with food or drink water represent a technological improvement in the delivery of the antigen, since, in addition to overcoming the problems associated with handling the same, facilitate strengthening the antigen when the animal immunity is below the threshold protective (Bucarey, Sergio et al. 2009).

Oral immunization has been an ideal vaccination strategy, as it has several advantages, among which we can mention the elimination of pain associated with an injection needle. Furthermore, oral vaccines offer important benefits, including safer administration since they allow to avoid risks associated with the use of hypodermic needles. The most immediate advantages relate to the ease of use and application.

Additionally, oral vaccines allow to avoid some difficulties arise when vaccines parenteral, such as granuloma formation at the injection site via used. These granulomas often affect the quality of the meat, so a vaccine to prevent this serious complication greatly valued in the related field of application. Furthermore, a vaccine of oral administration avoids the complications associated as a possible break of the injection needle during the vaccination process, deformation of the needle after successive uses which prevents a homogeneous vaccination in cattle (usual in this area parenteral vaccination with hypodermic syringes automatic pistol), disease transmission by contaminated needles, costs associated with livestock handling errors in the vaccination procedure, such as involuntary autoinoculation operator, and stress animal. The deposit of foreign bodies in the animal's flesh, caused with this type of vaccine also produces the consequent diminution of the quality of the meat of the vaccinated animal and associated economic losses.

From the immunological point of view, oral immunization has the ability to induce protective immunity in the area of a mucosa, via natural pathogen infection. This immunity is more difficult to achieve by immunizing parenterally. Furthermore, an oral vaccine has the advantage of being effective in containing the spread of infection and induce humoral and cellular immunity.

Despite the useful and promising is the use of an oral vaccine, only some of these vaccines have been developed and have managed to reach the market. The main cause of the above, relates to the active agents generally pharmaceuticals pose a significant problem when passing through the digestive system of an animal, that is, are completely inactivated or gradual. This is because the active compound, which corresponds to the antigen in the case of a vaccine as herein proposed, is degraded during transit along the digestive tract. The stomach of an animal is an extraordinarily inhospitable environment for these active compounds, since it has an extremely low pH (pH=1-2) and proteolytic enzymes whose function denature and degrade proteins. Product of the above, the antigen is modified before contact immuno sensitive cells associated lymphoid tissue to a mucosa (MALT). To solve the above problems, a transient change in the pH of the stomach, neutralization of gastric enzymes and/or stimulation of the immune response mucosal necessary. Another way to solve this problem is to provide a vehicle for oral administration to protect the antigen during transit through the stomach, however, to date most have been unsuccessful attempts used and have not been successful commercially. Additionally, one should consider that, in general protection vehicles tested and/or tested that are able to withstand the passage through the digestive tract have an inefficient release in MALT. Furthermore, there is also a tendency for the MALT of inducing immunological tolerance, because the antigen is denatured before contact with the "therapeutic target", where this corresponds to associated lymphoid tissue lining of the intestine (Peyer's patches). This implies the need to increase the number of doses and antigen concentration to exert the effect desired immunity, with a corresponding increase in costs. A better understanding of the operation and regulation of the mucosal immune system, along with the development of nanotechnological systems efficient release would address the problems mentioned and resolve the difficulties generated by the denaturation and release of antigen, and additionally, create a platform for generating oral mucosal vaccines which could be used for various types of persistent pathogens in livestock and veterinary industry in general.

Importantly, in recent years, encapsulating antigens and active compounds in micro particles using natural polymers such as chitosan and/or alginate or synthetic polymers have generated a solution to the problem present in oral vaccines, allowing develop an oral immunization format economically and effectively. This is because the use of microparticles (MPs) biopolymer protects the antigen from degradation (enzymatic and acid) and retains the biological activity along the digestive tract, which also allows it to be more efficiently endocytosed by M cells of Peyer's patches. Once the microencapsulated antigen is captured and processed by dendritic cells and resident macrophages, presentation and lymphocyte activation occurs, resulting in a humoral immune response and/or efficient cell in terms of intensity and duration respect immunity conferred by the antigen unencapsulated.

In the state of the art, it is known that chitosan is one of the most abundant biopolymer in nature after cellulose. Chitosan, poly β-(1,4)-2-amido-2-deoxy-D-glucopiranosal is a deacetylated chitin derivative, formed by N-acetylglucosamine units (GlcNAc). This biopolymer is obtained from the alkaline deacetylation of chitin and is a natural and linear cationic copolymer consisting of D-glucosamine units deacetylated and N-acetyl-D-glucosamine randomly distributed. Furthermore, chitosan has properties such as safety ($LD_{50}$>16 g/Kg), biocompatibility, is biodegradable and is biostimulant. Naturally occurs in the class *Zygomycetes fungi*, algae *Chlorella*, insect cuticle, cell walls of some plants, annelids and exoskeleton of crustaceans and molluscs.

It is also known that chitosan can be obtained industrially at low cost, also presenting other characteristics, such as antimicrobial activity, mucoadsortiva capacity and ability to open tight intercellular junctions (tight junctions). These qualities, coupled with the ability to bind proteins and macromolecules reversibly, have made it an excellent candidate for the development of oral vaccines and delivery systems controlled drug.

Another property of chitosan is its versatile ability to be modified by functionalization reactions with chemical groups such as thiols (SH), sulfates ($SO_4^{2-}$), sulfonates ($SO_3^-$), phosphate ($PO_4^{3-}$), etc. In the prior art, you can be found related modified chitosan documents, such as U.S. Pat. No. 8,778,384, which discloses a microencapsulation method of oral vaccines, with emphasis on aquatic species, based on chitosan functionalized with methyl groups (–$CH_3$), dimethyls (–$(CH_3)_2$), trimetilos —$(CH_3)_3$ and carboxymethyl (—$OCH_2COO^-$)) so enhance mucoadhesiveness. In the state of art you can also be found in documents using chitosan oral vaccines, such as WO 2003/086454 which discloses oral vaccines comprising chitosan microparticles loaded with antigenic material of an infectious agent causing a respiratory disease in mammals or poultry to combat infectious respiratory diseases. The scientific publication "Microparticles Chitosan loaded With yeast-derived PCV2 virus-like particles elicit antigen-specific cellular immune response in mice after oral administration" (Bucarey, Sergio et al. 2014), discloses that chitosan particles are used both as a carrier and mucosal adjuvant for particle delivery "virus-like" (VLPs) derived from PCV2 virus yeast as an oral vaccine, in order to overcome the problems associated with parenteral administration.

While oral or mucosal vaccines are disclosed in these documents, none of them solves the technical problem of the invention proposed here, while working to protect the antigen in the digestive tract, as in the case of WO 2003/086454, but they fail to obtain a controlled delivery vehicle, based on a biomimetic model for a specific antigen, as achieved with the present invention improving the efficiency and quality of vaccine surprisingly.

Finally include chitosan has been functionalized with various groups, however, functionalization through sulfur groups (—SR), containing the element sulfur (S), so far not been made and used with a biomimetic concept in treatment of diseases generated by viruses cell receptor using the HS. Use of PMs based polymer functionalized with structural similarity to a cellular receptor could generate a great interest in the pharmaceutical industry because chitosan functionalized thus may allow improved mucoadhesive (given by a high affinity for mucin), a higher permeability, stability and greater control over the release of antigens and drugs to mucosal level. Also, other biopolymers comprising units D-glucosamine and/or N-acetyl-D-glucosamine such as chitin with structural similarity to heparan sulfate, and functionalized sulfur atoms, also may permit improved mucoadhesive, and a higher permeability, stability and greater control over the release of antigens and drugs and greater control over the release of antigens and drugs to mucosal level.

According to the above, the present application aims to provide a pharmaceutical product intended to solve the problems described in the prior art related to administration parenterally, by vaccination mucosal based on a biomimetic model, orally administered or intranasal, allowing deliver the antigen or active compound in a controlled manner without being degraded during transit along the digestive tract. Notwithstanding the above, the vaccine may also be administered parenterally.

OBJECT OF THE INVENTION

Productivity of livestock, agricultural industry and animal husbandry is affected by various diseases which can be prevented by vaccination, usually parenterally, however, vaccination parenterally has drawbacks and/or disadvantages related to direct costs and indirect associated with this type of vaccine, such as time, labor and infrastructure, induction of the inflammatory response and inclusion of foreign bodies in the injection site and stress derived from animal management.

The present invention proposes as a solution a product for the treatment and control of these diseases, more specifically a pharmaceutical product administration may be accomplished via mucosal (oral or intranasal) without impairing optionally be administered parenterally for effective disease control generated by pathogens such as viruses, using heparan sulfate (HS) as cell receptor by functionalized chitosan and controlled release mucoadhesive properties based on a biomimetic model. The pharmaceutical of the present application is a vaccine regardless of the route of administration, oral, intranasal or parenteral, can eliminate pain, inflammation and adverse effects of vaccines more traditionally employed.

The pharmaceutical of the present application is a product that can optionally be used as a vaccine mucosal, i.e., oral or intranasal administration, without impairing be administered parenterally, wherein the antigen is encapsulated in microparticles (MPs) chitosan functionalised with thiol groups and/or sulfates. Optionally, other biopolymers comprising D-glucosamine units, N-acetyl-D-glucosamine such as chitin with structural similarity to heparan sulfate, and functionalized sulfur atoms, may also be employed in embodiments of the present invention. MPs are prepared with a specific particle size and surface charge, where the ranges of particle size and surface charge are from 1 to 20 µm and −30 to +30 mV, respectively. Chitosan used in the present invention is not restricted to a specific molecular weight, that is, you can use a chitosan high, medium or low molecular weight, with viscosities may range from 200 to 800 cP, you can even use a chitosan a viscosity up to 2000 cP. However, the chitosan used for optimal results must meet the condition of having a degree of deacetylation greater than 50%. The preparation of PMs is performed by a biomimetic design, using as the cellular receptor structural biomodel HS, i.e. using antigens present in pathogens using macromolecules HS as a receptor to enter the host cell. Thus, it solved effectively the need for a vehicle to protect the antigen from degradation and which in turn is efficient in the controlled release of the same for presentation to cells of the immune system (MALT specifically) to give finally MPs functionalized chitosan also have an increased mucoadhesiveness with improved affinity for mucin. Surprisingly, by using the vaccine of the present application, a high rate of recovery of the antigen is obtained in step microencapsulation thereof, particular affinity indicating a higher binding capacity of chitosan functionalized sulfur atoms to specific antigens agent pathogen. This quality gives the functionalized chitosan of the present invention bioespecifies a chemical bond with the antigen obtained by recombinant DNA techniques. Such binding gives the vaccine of the present invention a property specific chelator for the infectious agent, which allows for greater antigen retrieval during vaccine production and simultaneously, once administered, greater control over the release antigen.

Accordingly, the vaccine of the present application comprising a microencapsulated antigen in modified chitosan, or other low molecular weight (LMW) biopolymers unit D-glucosamine and N-acetyl-D-glucosamine functionalized with thiolated or sulfated groups at 1% to 2%, can provide an effective, safe and delivery immunization controlled to white therapeutic, avoiding the problems associated with a managed vaccination by injecting while overcoming the problems associated with oral administration, i.e. can deliver the antigen or active compound in a controlled manner without being degraded during transit along the digestive tract. Notwithstanding the above, the vaccine may also be administered parenterally. The vaccine of the present application will control, prevent and treat diseases caused either by virususing HS as cell receptor in different types of livestock. The vaccine of the present application will control, prevent and treat these pathogens according to the type of animal:

TABLE A

Viral pathogens and prions using the HS as cell receptor:

| PATHOGEN | GENOME | GENDER | FAMILY | HOSP |
| --- | --- | --- | --- | --- |
| PCV2 | Single strand DNA | *Circovirus* | Circoviridae | Swine |
| PRRSv | Positive RNA | *Arterivirus* | Arteviridae | Swine |
| Peste porcina clásica (PPC) | Positive RNA | *Pestivirus* | Flaviviridae | Swine |
| Herpesvirus equino tipo I (EHV-I) | Double strand DNA | *Varicellovirus* | Herpesviridae | Equine |
| Herpesvirus equino tipo IV (EHV-IV) | Double strand DNA | *Varicellovirus* | Herpesviridae | Equine |
| Herpesvirus bovino tipo I (BoHV-I) | Double strand DNA | *Varicellovirus* | Herpesviridae | Bovine |
| Herpesvirus suino tipo I (SuHV-I) | Double strand DNA | *Varicellovirus* | Herpesviridae | Swine, among other species |
| Diarrea viral bovina | Positive RNA | *Pestivirus* | Flaviviridae | Bovine, swine, sheep, goat |
| PRPc Prion | | | | Bovine, sheep |
| Fiebre aftosa | Positive RNA | *Aphthovirus* | Picornaviridae | Bovine, sheep, swine, goat |
| Diarrea epidémica porcina (PED) | Positive RNA | *Alphacoronavirus* | Coronaviridae | Swine |
| Gastroenteritis transmisible del cerdo | Positive RNA | *Alphacoronavirus* | Coronaviridae | Swine |
| Enfermedad vesicular porcina (SVD) | Positive RNA | *Enterovirus* | Picornaviridae | Swine |
| Estomatitis Vesicular (VSV) | Negative RNA | *Vesiculovirus* | Rhabdoviridae | Bovine, equine, swine |
| Peste porcina africana (ASFV) | Double strand DNA | *Asfivirus* | Asfarviridae | Swine |

Note that obtaining the vaccine of the present invention, it should be simple and inexpensive, because the reagents and the preparation steps thereof are simple and inexpensive. Furthermore, the preparation method produces high yields due to the high recovery of antigen after its overexpression, obtaining an efficient product (chelator property). In this sense, the solution provided by the present invention corresponds to a mucosa vaccine that is innovative product, that to date does not exist on the market, which serves for the effective control of infectious diseases produced by virus that affect the livestock industry and is an alternative to vaccines administered parenterally available today, besides being a vaccine has an effect controlled release of antigen, easy to handle and produces no injury and stress in vaccinated animals.

DESCRIPTION OF FIGURES

FIGS. 9A-D. Profile of viral load in pigs immunized against PCV2 according treatment. (A) Group 1 and 3. (B) group 2 and 4. The black bar corresponds to the statistical average.

FIG. 10. Sulfated chitosan concentration effect over the PCV2 viral title.

FIG. 11. Sulfated chitosan molecular weight effect over the PCV2 viral title.

FIG. 12. Sulfated chitosan effect over the PCV2 viral title

DETAILED DESCRIPTION OF THE INVENTION

Figure 1A:
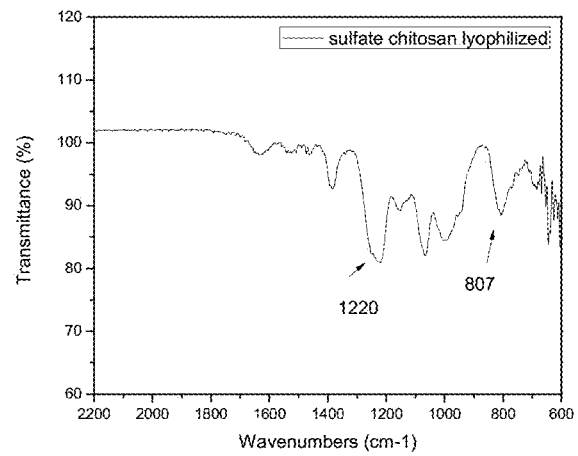
FIGS. 1A-1B illustrate the infrared spectra (FTIR) obtained for sulfated chitosan (QS) (1A) and thiolated chitosan (QT) (1B) using a FTIR-ATR (Interspectrum-200×) spectrophotometer.

As mentioned, the main objective of the present invention is to provide a pharmaceutical, more specifically a vaccine for parenteral administration or via mucosal (oral or intranasal), for controlling diseases generated by infectious agents such as viruses, using the HS as cell receptor and affecting the livestock industry according to the above in Tables a, B and C.

The vaccine of the present application comprises a receiver for the HS antigen encapsulated in a vehicle which allows the antigen is administered orally or subcutaneously. Wherein said antigen is encapsulated efficiently chitosan modified either by thiolation or sulfation optionally other low molecular weight (LMW) biopolymers unit D-glucosamine and N-acetyl-D-glucosamine functionalized with thiolated or sulfated groups at 1% to 2% also modified allowing oral administration remedying the problems associated with vaccine administered via parenteral, allowing the antigen to be delivered, without this being degraded during transit along the digestive tract and which allows a controlled antigen release. The vaccine of the present application has the following composition: Each 2 mL of the vaccine contains from 12 to 50 µg of the antigen.

As an example and not limiting to the present application, the scope and advantages of the immunogenic vaccine of the present invention based on a type of disease affecting animal health is hereby described. However, it should be remembered that the vaccine of the present application also can be used to control, prevent and treat other diseases such as those mentioned in Tables A described above, that is, diseases caused by some other viruses, that use macromolecules such as sulfated polysaccharide as HS cell receptor. For instance, the porcine circovirus or PCVAD caused by porcine circovirus type 2 (PCV2) has a huge economic impact on the global swine industry (Bucarey, Sergio et al. 2009). It is characterized to use HS as cell receptor during the infection. In addition to improving management and management practices (best standards of biosecurity and production), availability of vaccines against PCV2 represents an effective immune option to mitigate the impact of these diseases.

EXAMPLES

Example 1. Optimized Formulation of the Vaccine of the Present Application

The biological properties of chitosan (Q) is improved by functionalization with compounds carrying sulfate groups, and thiols, allowing give the chitosan (Q) an increase in mucoadhesiveness and bondability to the protein, in this case Cap PCV2. This functionalization allows a Q functionalized with greater control over the release of viral antigens to mucosal level, especially by improving affinity for mucin and structural similarity to the HS, in this case, the natural cellular receptor PCV2 virus.

For experimental studies, is synthesized Q sulfated (QS) and thiolated (QT) from Q according to the chemical characteristics described commercial chitosan (QC), in order to formulate PMs loaded with antigen Cap PCV2 (from a national isolated) by spray drying.

Thus, it is possible to obtain PMs QS, QT and QC where Cap protein of PCV2 virus, assembled as VLPs in yeast, under two formulations (A and B) of different concentrations, one with double the concentration that is entered the other, which are described as 1× and 2× as explained below. PMs were characterized by FTIR, light scattering and zeta potential, confirming the functionalization of Q, particle size and surface charge of the PMs. Additionally, the degree of affinity of the PMs by mucin measured. Finally, it is possible to detect and quantify the presence of protein in each formulation Cap, concluding that PMs based on QT and QS showed greater capacity for interaction with antigen VLP PCV2 regarding PMs formulated QC.

Example 2. Functionalization of Chitosan

QT is synthesized using thioglycolic acid ($C_2O_4SH_2$) in the presence of 1-ethyl-3-(3-dimethylaminopropyl) carbodiimide (EDAC) as a catalyst. Moreover sulfation of Q is performed in the presence of sulfuric acid ($H_2SO_4$) as a surfactant agent.

Example 3. Thiolation Chitosan (QT)

For thiolation of Q a method described by Anitha et al 2011 is used. For this, 1 g of Q with viscosity between 20 and 300 cP is dissolved in 100 mL of acetic acid solution 1%. Subsequently, add 2 mL of 125 mM EDAC in aqueous solution, under magnetic stirring. Then, 1 g of thioglycolic acid is added and the pH adjusted to pH=5 with a 1M NaOH solution. The resulting mixture is incubated for 4 hours in the dark, under magnetic stirring at room temperature. The obtained solution is dialyzed in cellulose membrane with pore size 3.5 kDa, in dark at 4° C. for 4 days, against the following solutions: 5 mM HCl (1st day), 5 mM HCl+1% NaCl (2nd and 3rd day) and 5 mM HCl (4th day). Finally, the content of QT is lyophilized and chemically characterized.

Example 4. Sulfation of Chitosan (QS)

For sulfating Q a method described by Naggi et al was used. 1981. For this, 1 g of Q with viscosity between 20 and 300 cP is dissolved in 40 mL of $H_2SO_4$ precooled to 4° C., is kept under stirring for 2 hours. Subsequently, this mixture is precipitated dropwise into 250 mL of cold ethyl ether, under constant stirring. Then filtered in filters of porous glass, washed with abundant cold ethyl ether and the product collected unfiltered, adding it to 100 ml of nanopure water, previously cooled to 4° C. Immediately thereafter, the pH is adjusted to 7.6 with an aqueous solution of NaOH cooled and dialyzed in cellulose membrane with pore size 3.5 kDa for 3 days at room temperature against nanopure water. Finally, the product obtained is subjected QS to evaporation in an evaporator with reduced rotary machine (Heidolph Laborotta 4001 Efficient) pressure, to obtain approximately 10 mL, which are lyophilized and chemically characterized.

Example 5. Spectroscopic Characterization FT-IR

Functionalized Q were characterized by infrared spectroscopy using an FTIR-ATR (Interspectrum-200×) spectrophotometer. FIG. 1A shows the spectrum obtained for lyophilized QS, where absorption bands are observed at 1220 and 807 $cm^{-1}$ corresponding to the C—O—S and S=O groups respectively, confirming that the sulfation reaction is successful.

Figure 1B:
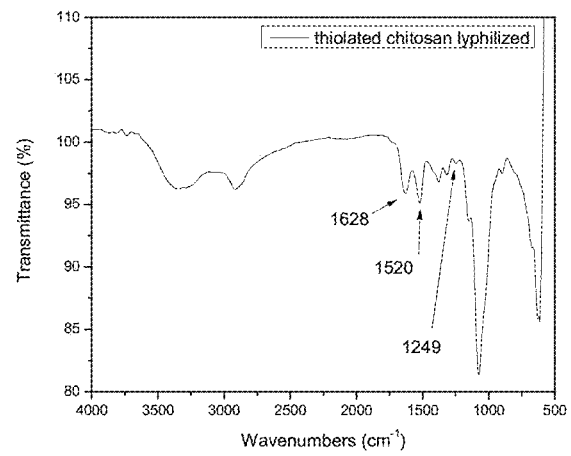

FIG. 1.B shows FTIR spectrograms obtained for lyophilized QT, which has absorption bands at 1628, 1520 and 1249 $cm^{-1}$, which confirmed the presence of amide I, amide II and the thiol group, respectively, indicating that the thiolation reaction it is successful.

Figure 2:
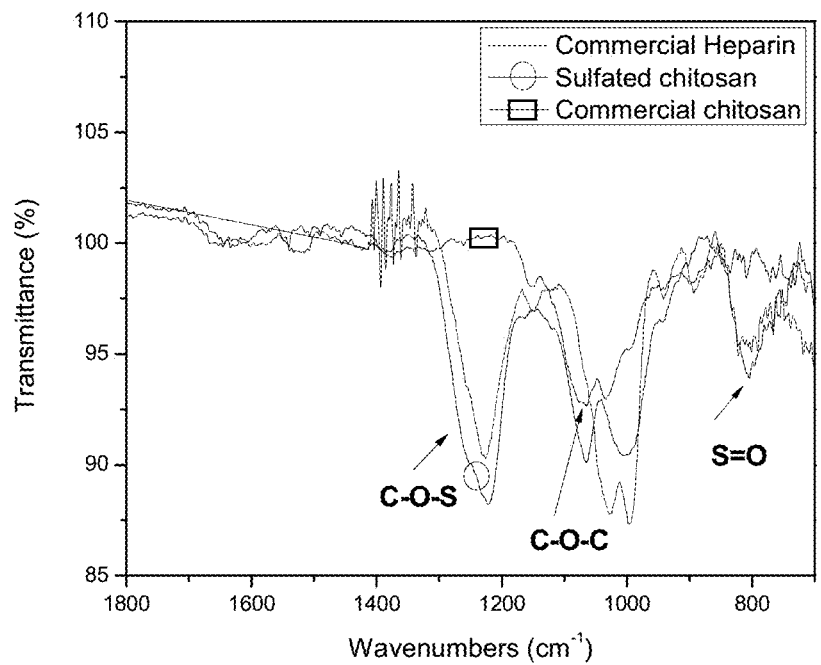
FIG. 2 illustrate FTIR spectrum of commercial heparin, commercial chitosan and chitosan sulfated. Matching peaks are observed at the wavelengths 1220 $cm^-$, 1073 $cm^{-1}$ and 807 $cm^1$, attributable to the links S=O, C—O—C and C—O—S, respectively.

They were also compared the QS with commercial and heparin Q business. FIG. 2 shows the FTIR spectrograms obtained for commercial heparin, commercial chitosan and chitosan sulfated where matching peaks observed in the wavelengths 1220 $cm^{-1}$, 1073 $cm^{-1}$ and 807 $cm^{-1}$, attributable to the links S=O, C—O—S, respectively.

Example 6. Production and Quantification of Antigen

In the case of antigen VLP PCV2, this is prepared by generating a culture of *Saccharomyces cerevisiae* strain N30 transformed with a plasmid carrying a DNA sequence coding for the gene product or protein of interest under a galactose-inducible promoter (Bucarey, Sergio et al. 2009).

For this particular example the optimized sequence SEQ ID No was used.: 1 PCV2 ORF2 gene (Bucarey, Sergio et al. 2009):

This nucleotide sequence encodes a protein with the amino acid sequence SEQ ID NO: 2.

This viral antigen corresponding to any viral protein of a circovirus capable of eliciting an immune response in the animal, selected from the protein of the viral capsid, such as proteins such virus (Bucarey, Sergio et al. 2009). For example, with plasmid pYES: opt-cap, expressing an optimized version of PCV2 cap gene under a promoter inducible by galactose. This procedure is used to produce antigens VLPs PCV2 standardized manner, according to previously described by Bucarey et al., 2009. Subsequently, cells were lysed by a type Bead Beater homogenizer, mixing a volume of approximately of 200 μL of lyophilized yeast by the same volume of beads of 1 mm zirconia in a standardized milling time of 4 minutes.

To obtain an estimate of the amount of antigen is performed one dotblot lysate sample at a concentration of lysate 5.36 mg/mL. Briefly, once the samples to nitrocellulose membranes transferred, incubated in a blocking solution (skim milk 5% Tween-20 (monolaurate polyoxyethylene sorbitan) 0.05% dissolved in PBS buffer pH salicylic phosphate, for 1 hour at room temperature, then incubated with an antibody anti-PCV2 pig diluted 1:50 in blocking solution for 2 hours at 37° C. Subsequently, the membrane 3 times with PBST (PBS-Tween 20 wash 0.05%) for 5 minutes, and then be incubated for 2 hours at 37° C. with secondary antibody anti-pig IgG (Millipore) diluted 1:. 5000 in blocking solution. Finally, the membrane is washed 3 times 5 minutes each with PBST, then reveal with cloronaptol (One step Thermo Scientific) and observe the appearance of signals (dots).

Figure 3:
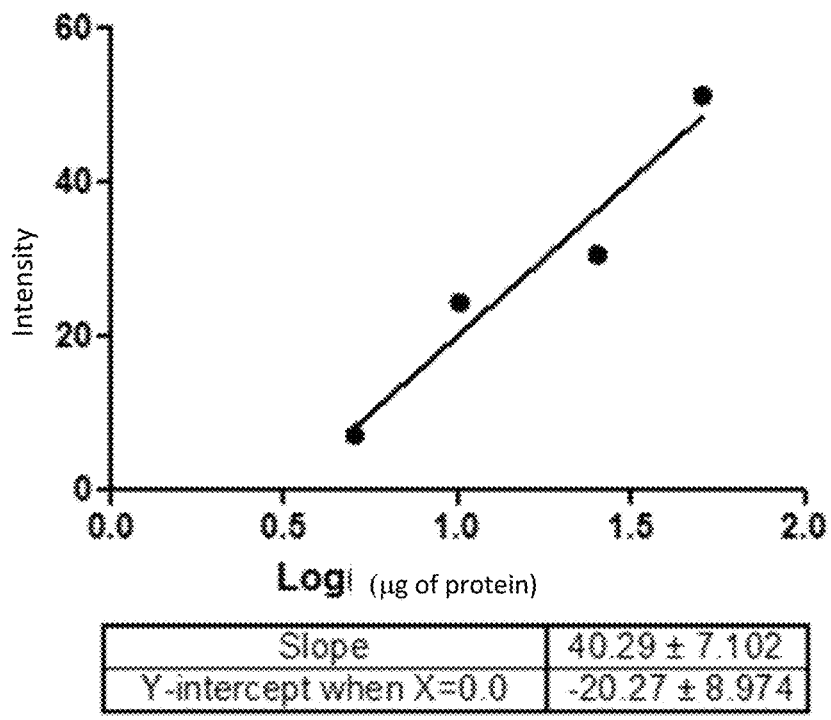
FIG. 3 illustrate curve and equation of the line constructed using a second commercial single-dose vaccine CircoFLEX, as standard, containing purified circovirus antigen (PCA™) adjuvanted with ImpranFLEX™, aqueous carbomer-based adjuvant. Shows the equation used to interpolate the amount of protein in each point corresponding to the lysate of recombinant yeast.
Figure 4:
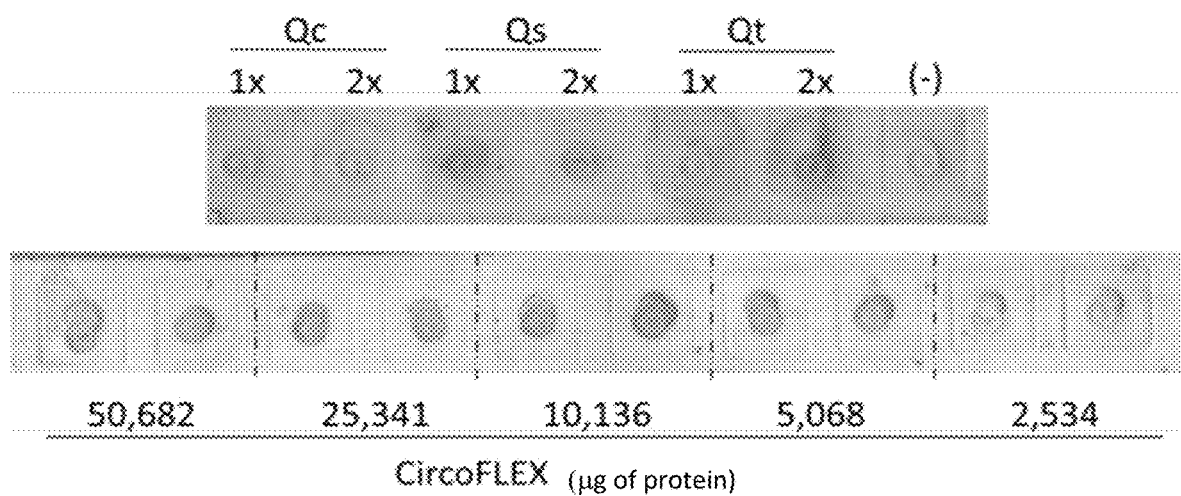
FIG. 4 illustrate Dotblots of chitosan PMs loaded with PCV2 VLP antigen, shows PMs treated with 1N HCl at 90° C. for 10 minutes. Standard different amounts of protein of commercial PCV2 vaccine were used.

To generate an estimate of the amount of quantization in each lysate antigen, a parallel calibration curve with serial dilutions of the commercial vaccine mentioned as standard antigen Cap is constructed. For this the amount of protein was quantified by BCA method (bicinchoninic acid), determining an initial concentration of 1013.73 μg/mL. Serial dilutions standard are added for points with different intensities, which are analyzed by densitometry with the program "ImageJ" (Schneider, C. et al., 2012), allowing a calibration curve and obtain an equation of the line (FIG. 3).

Example 7. Formulation of Microparticles (MPs)

The formulation of PMs Q functionalized and unfunctionalized, are made using the technique of spray drying using a Büchi Mini Spray Dryer equipment B-290. All materials used are previously sterilized by autoclaving. A solution of QS 1% to which is added subsequently antigen corresponding to crude extract of recombinant yeast containing overexpression optimized gene product of ORF2 gene of PCV2 virus, which corresponds to a protein capsid virus is prepared and that, in the conditions in which it is carried out the production assembled spontaneously VPLs (its acronym, "Viral Like Particles"). For this illustrative case, the formulation called 2× corresponds to 750 mg of crude extract of yeast containing the antigen dissolved in deionized water to a final volume of 70 ml.

In the case of the formulation called IX it is diluted with a dilution factor of 2, the 2× formulation. The mixture is covered with gauze and parafilm to avoid contamination and under stirring in a homogenizer (Heidolph RZR 2051 Control) at 1.510 rpm for 60 min at 5° C. Without stopping the stem take an aliquot (2 mL) of the mixture, to calculate then EE (encapsulation efficiency) of total protein at this point in the process (Corresponding to the pre-encapsulation). Finally, the stirring is stopped and the stem is removed under biosafety hood. Subsequently subjected to spray drying using the following parameters: temperature (T°) input: 140° C., T° output: 60-90° C., Percentage (P°) aspiration: 100%, $P^{o1}$ atomizing: 300 Nl/h, nozzle diameter: 0.7 m.

After the spray drying process, the PMs are collected under biosafety hood and refrigerated at 4° C.

Example 8. Quantification of VLP Antigen PCV2 Chitosan Microparticles

Subsequently, to determine the amount of antigen microencapsulated in formulations of PMs based on the type of Q used, other dotblot series of PMs commercial Q, QS and QT, loaded with antigens at a concentration IX and 2× (FIG. 3) is performed. To perform the dotblot 17.5 mg of each formulation PMs corresponding to the standardized amount was weighed to obtain a dose of 30 mg/mL, slightly lower than described by Bucarey et al., 2014, and diluted in 300 μL 1N HCl. Then heated to 90° C. for 10 minutes and 300 μL of 1N NaOH is added. Subsequently, centrifuged and the supernatant 200 μL per sample is analyzed. For the standard curve of the commercial vaccine, the same μg protein determined in the previous dotblot used. As a result a percentage was obtained by antigen microencapsulation in the range of 0.01 to 0.05%. In each formulation, which joined as much antigen were QS IX and 2× QT, with a ratio of 0.47 and 0.44 μg of antigen per mg of PMs, respectively (Table 1), which was determined the preferred concentration is 0.24 μg is per 1 mg of antigen PMs.

TABLE 1

Quantity of PCV2 VLPs antigens in PMs.

| Formulation | Quantity of antigen by dot (mg) | Weight of MP obtained for each formulation (mg) | Total of antigen obtained per mg of MP (mg) |
|---|---|---|---|
| MPsQC 1X | 0.8459 | 261 | 0.15 |
| MPsQC 2X | 0.5314 | 240 | 0.09 |
| MPsQT 1X | 2.7446 | 200 | 0.47 |
| MPsQT 2X | 1.3804 | 260 | 0.25 |
| MPsQS 1X | 0.7502 | 250 | 0.13 |
| MPsQS 2X | 2.5487 | 230 | 0.44 |

Example 9. Determination of Encapsulation Efficiency (EE %)

To calculate the protein content encapsulated in PMs, pre- and post encapsulation aliquots were analyzed, using the colorimetric detection method Bradford protein. For this, an aliquot of the formulation was removed before the encapsulation, elapsed stirring for 1 hour (pre aliquot encapsulation). Then, a given sample of the PMs formed was dissolved in distilled water 1 mide (post encapsulation aliquot). Subsequently aliquots to 1.470×g for 10 minutes and centrifuged protein concentration in the supernatant is measured by spectrophotometry (UV/VIS Spectrophotometer double beam (Rayleigh UV-2601)) to λ (wavelength) of 595 nm, calculating EE in triplicate according to Equation 1. To calculate EE is considered that the total protein corresponds to the concentration of protein present in the pre encapsulation aliquot, and the encapsulated protein is obtained by difference between total protein and concentration free protein present in the supernatant in the post encapsulation aliquot.

The encapsulation efficiency (EE %), value expressing the protein content encapsulated in PMs, and is calculated according to the following formula:

EE %=(amount of encapsulated protein/Number of Total protein)×100            (1)

The results of the three types of PMs Q obtained are shown in Table 2. The values of the various formulations EE above 90% have values. Furthermore, EE values obtained for the same formulations include, but using a smaller amount of crude yeast extract, which contains the antigen PCV2 (1×) (half the mass of the antigen used in the previous point, assigned as 2×) to have a point of comparison. EE results for the concentration of 1× are seen in Table 3. DS values ranged between 1× and 2× formulations, being higher for 2×, because the latter contain a higher amount of protein available for encapsulated. According to the results obtained for EE 1× and 2× concentrations 2× formulation was selected to continue the analysis and subsequent determinations.

TABLE 2

Values of encapsulation efficiency (EE %) for PMs QC, QT and QS in their formulations 2X.

| Formulation | EE (%) |
|---|---|
| MPQC 2X | 94.13 |
| MPQT 2X | 95.36 |
| MPQS 2X | 90.31 |

TABLE 3

Values of encapsulation efficiency (EE %) for PMs QC, QT and QS in their formulations 1X.

| Formulation | EE (%) |
|---|---|
| MPQC 1X | 69.91 |
| MPQT 1X | 95.36 |
| MPQS 1X | 82.23 |

Example 10. Morphological Analysis by Scanning Electron Microscopy

Figure 5:
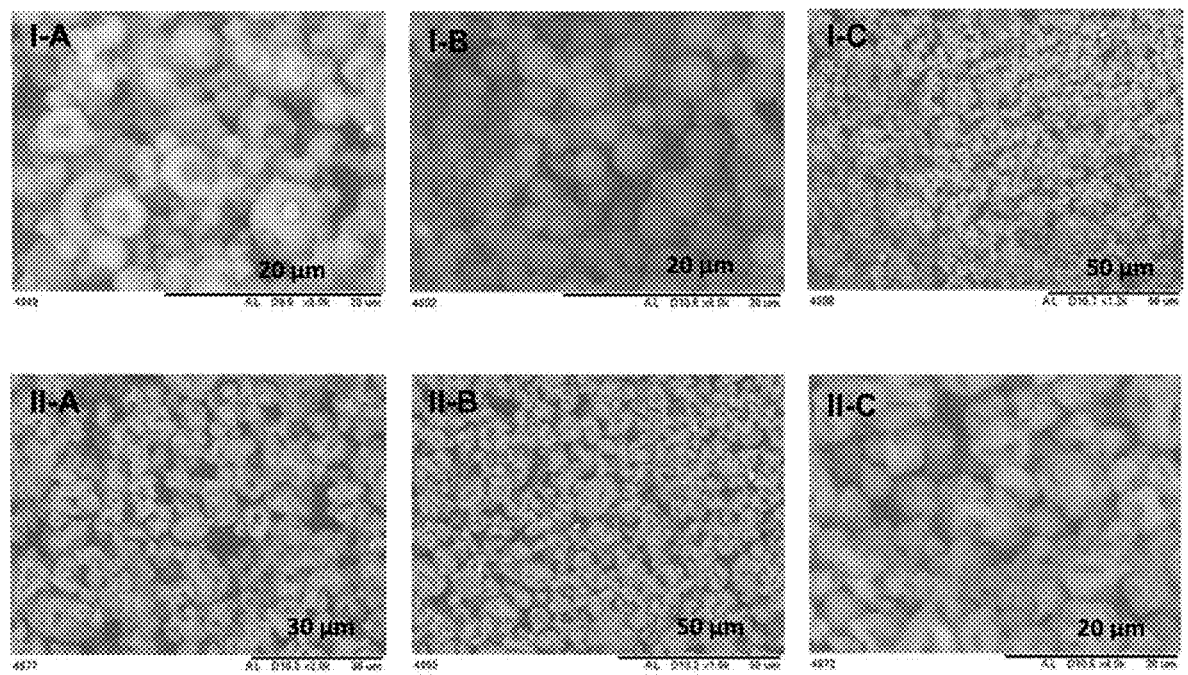
FIG. 5 illustrates comparative SEM images of PMs made of QT, QC and QS formulated by spray drying without load (I), and loaded with crude extract of recombinant yeast expressing PCV2 antigen (II). A MPQT; B and C MPQC MPQs.

MPs uncharged and charged with 2× antigen were analyzed by scanning electron microscopy (SEM) on a micro-scope Hitachi Tabletop™ 3000 coupled to a device elemental microanalysis EDS QUANTAX 70. As seen in FIG. 5, the formation was confirmed PMs. All PMs have more or less spherical shapes and edges, and sizes ranging from 1 to about 20 μm. Formulations without antigen presenting a smoother surface than the charged antigen tends to be roughened collapsed surface.

Example 11. Determining the Size and Zeta Potential (ξ)

To make this determination, an average size of PMs unloaded and loaded with crude extract of yeast by the technique of dynamic light scattering (DLS) in a particle size analyzer (90 Plus/BI-MAS) is estimated. In addition, the average PMs unloaded and loaded with crude extract of yeast on a Zeta Plus zeta potential-Brookhaven Instruments (ξ) is measured (see Table 4). PMs QC and QT showed positive charges due to the presence of amino groups ($-NH_2$) in its protonated chemical structure in solution. PMs composed QT exhibit less than QC formulated with positive charge, the above is explained by the presence of thiol groups (—SH) partially conjugates compared to $-NH_2$ groups on its structure. MPs composed SC presented net negative charge due to the presence of sulfate groups ($OSO_3^{2-}$) It is further noted that the load is changed depending on the amount of incorporated antigen PCV2 (crude yeast extract presents −21.27 mV negative charge), decreasing net charge at the positive and negative charged particles with antigen. As for determining the effective diameter, unloaded MPs had average sizes smaller than the antigen-loaded MPs. In general, all PMs had mean sizes less than 10 μm, which allow absorption thereof by the M cells present in Peyer's patches of the intestinal epithelium. Thus, the functionalized Q PMs would contact dendritic cells, promoting the development of an immune response.

TABLE 4

Effective diameter and zeta potential (ζ) of chitosan microparticles for 2X.

| | Effective diameter (nm) | Zeta potential (mV) |
|---|---|---|
| Formulation 2X | | |
| MPQT | 9.109.3 (±691.5) | +27.09 (±0.42) |
| MPQC | 5.435.6 (±558.2) | +33.66 (±0.69) |
| MPQS | 1.285.5 (±33.7) | −14.66 (±0.62) |
| Formulation without antigen load | | |
| MPQT | 2.526.1 (±1.096.6) | +30.96 ±0.80) |
| MPQC | 3.220.7 (±1.317.4) | +38.50 (±1.67) |
| MPQS | 658.6 (±20.7) | −35.97 (±0.92) |

Example 12. Mucoadhesivity Test

To determine and optimize the mucoadhesive properties of PMs a study of the interaction between these and the type 1 mucin (bovine submaxillary gland) and type 3 (from pig stomach) is performed. For this, 100 mg pf PMs are weighed and added 500 μL mucin solutions (2 mg/mL) at pH 5. Following this, it is incubated to 100 rpm at 37° C. for 1 hour. Then centrifuged at 4.000×g for 2 minutes, the supernatant is removed and measured in a UV-Vis spectrophotometer using the colorimetric detection method BCA protein). Measurements are performed in triplicate. Table 5 shows the (μg) amounts of mucin member PMs calculated as the initial mucin detected in the solution minus the free mucin present in the post-centrifugation supernatant.

TABLE 5

Test mucoadhesive. Amount of mucin adhered to 10 mg of MPs. These values were calculated by difference between the concentration of mucin detected in the initial solution (2 mg/mL) and the concentration of free mucin supernatant.

| MPs | Mucine type 1 adhered to Mps (μg) |
|---|---|
| MPsQC | 88.47 |
| MPsQT | 120.00 |
| MPsQS | 102.31 |

The results obtained with mucin type 1 show high mucoadhesiveness QT and QS QC respect to their interaction with PMs, with over 140% of mucoadhesiveness values. In turn PMs functionalized with sulfur groups, especially with thiol groups present greater mucoandesividad that PMs Q unfunctionalized, can also be explained by the formation of covalent linkages, disulfide bridges (S-S) between rich residues cysteine present in the mucin and sulfur-containing groups of MPs. According to the results shown above, PMs have values above 90% EE and sizes of 1 to 9 μm. In turn, the MPs composed of QS presents net negative charge, and PMs composed of QT and QC have net positive charge.

Example 13. Preclinical Trials in Mice

In order to determine the efficiency of the vaccine of the present invention, preclinical trials using QT and QS PMs loaded with the cap corresponding to the protein of PCV2 virus antigen were performed.

The composition preferably used in these trials was ≥12 μg of VLPs ORF2 antigen Porcine circovirus type 2 per 2 mL product.

Preclinical trials were conducted in mice to evaluate the efficacy and safety of PMs contained in the present invention, using different routes of administration. The immunogenic potential of the product of the present invention was tested in BalbC mice after administration of PMs QS, QT and QC loaded with antigens in 2×PCV2 formulation, oral, nasal and injectable route.

Figure 6:
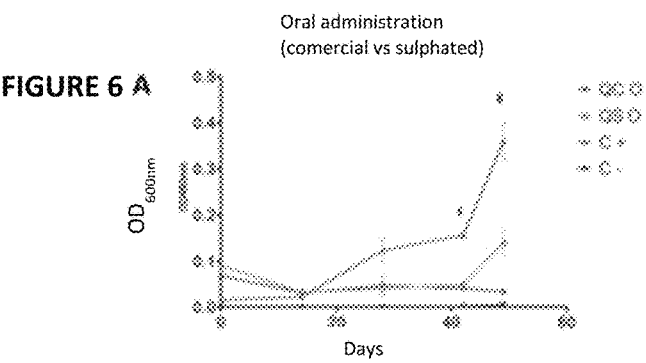
FIGS. 6A-6F. illustrate the profiles of specific anti-PCV2 associated with IgG from mice immunized by oral, intranasal (C and D) and subcutaneous (E and F) of sulfated chitosan microparticles (QS), thiolated chitosan (QT) and commercial chitosan (QC) loaded with PCV2 antigens.

The results of in vivo experiments show that when comparing the experimental formulations with a second commercial vaccine—subunit vaccine inactivated porcine circovirus type 2, vector dead baculovirus containing Microsol and Diluvac forte as adjuvants, vaccines formulated based on QS and QT, administered orally (FIGS. 6A and 6B, respectively), have a profile similar to induction of the commercial vaccine efficacy (defined as the total amount of IgG anti-PCV2 experimental day 50) antibody. The same comparison shows similar results for the intranasal route (FIGS. 6C and 6D) vaccine formulated based on QT and QS. Additionally, the experiments demonstrate that oral administration of vaccines formulated based on QT and QS stimulates the induction of serum antibody 4 to 5 times more efficiently than QC.

Furthermore, in order to evaluate the safety of these vaccine formulations also were administered subcutaneously (FIGS. 6E and 6F), was determined that the vaccine of the present application no adverse effects associated with QC and commercial vaccines reported, such as necrotizing dermatitis. That is, the vaccine of the present invention has a higher efficiency compared to the commercial vaccine QC and also solving the problems associated with vaccine administered parenterally.

Accordingly, these results show that using Q functionalized a safe and simple system for the delivery of viral antigens PCV2 is provided, and thus, the administration via oral or nasal can be a safe effective alternative strategy to induce efficiently antibodies.

To measure the safety of the formulation was injected subcutaneously in experimental animals, showing local lesions at the site of administering the vaccine to the QC (subcutaneously) at day 7 post immunization. These lesions were maintained in the time until the end of the test. The animals showed clinical signs of systemic involvement or response to pain. The observed local lesions were classified into two groups: ulcerative and nodular lesion.

According to the degree of injury score, which is detailed below is assigned.

TABLE 6

Degree of injury vs. Score assigned for an ulcerative lesion.

| Score | Lesion |
|---|---|
| 0 | Without visible lesion |
| 1 | Visible ulcer with diameter less than 0.3 cm |
| 2 | Visible ulcer with diameter more than 0.3 cm |

TABLE 7

Degree of injury vs. Dular score assigned for injury.

| Score | Nodular lesion |
|---|---|
| 0 | Without visible lesion |
| 1 | Visible nodule with diameter less than 0.3 cm |
| 2 | Visible nodule with diameter more than 0.3 cm, 2 or more nodules |

In Table 8 the scores assigned to the lesions observed in individuals who were treated with PMs QC loaded with antigen (MPQC) via subcutaneous. All individuals in this group had local lesions at the site of application of the vaccine, coinciding with ulcerative lesions of alopecic, scabby and limited aspect.

TABLE 8

Points assigned to ulcerative lesions in animals treated group MPQC.

| Individual | Score of ulcerative lesion |
|---|---|
| 1 | 2 |
| 2 | 2 |
| 3 | 2 |

In Table 9 the scores assigned to the lesions observed in individuals who were treated with PMs QT (MPQT) and PMs QS (MPQs) loaded with the antigen are shown. In this case they showed no focal nodular lesions mobile hard consistency in the application site of the vaccine.

TABLE 9

Score assigned to nodular lesions in animals treated group MPQT (A) and MPQs (B).

| Individual | Score of ulcerative lesion |
|---|---|
| 1A | 0 |
| 2A | 0 |
| 3A | 2 |
| 1B | 0 |
| 2B | 1 |
| 3B | 0 |

These results demonstrate that by using Q functionalized insurance system easy to use for controlled delivery of antigens to mucosal level is provided, and thus, their oral and nasal delivery is an alternative strategy to efficiently induce antibodies. The efficacy of the vaccine is based on a proposal biomimetic model, achieving a controlled release effect and highly desired in the pharmaceutical industry and obtained in the present invention prolonged activity, as shown in the following test:

Example 14. Study of In Vitro Release of Antigens

To carry out the study in vitro release of the total protein contained in the vaccine formulations of the present application, they weighed 5 mg PMs QC, QT and QS, loaded with crude yeast extract containing an antigen of Porcine Circovirus (PCV2). Then, 1 mL of the following solutions were added: PBS pH 7.4; gastric fluid simulated pH 1.2 and simulated intestinal fluid at pH 6.7. Both simulated fluids reagents are obtained from Fluka®Analytical (Sigma-Aldrich). Then, all mixtures are agitated by vortexing, and incubated in water bath thermostated at 37° C. with constant movement to 135 rpm for 15 hours. At various times (0, 0.5, 1, 1.5, 12 and 15 hours), the PMs are centrifuged at 14.240×g for 5 minutes. Then the protein content in the supernatant from each tube is estimated using the Bradford Plus (Coomassie Plus™ Protein Assay Reagent) method in conjunction with UV-Vis spectrophotometry at a specific wavelength 595 nm. Subsequently, the MPs are immersed in the bath thermoregulated again until the next sampling.

The total volume of each solution in the tubes was maintained constant during the test by adding an equivalent extracted from the sample volume under study. Finally, the determination of the cumulative amount of protein released from total PMs is performed using a standard calibration curve. The release kinetics of the protein from the PMs contained seen in FIGS. 6A-6F. The average protein concentration released is expressed in concentration units μg/mL.

The MPQC, MPQs and MPQT exhibit release kinetics very similar protein in PBS, which is used as control (see FIG. 6A) with a maximum release of proteins (140-160 μg/mL) at approximately 12 hours into the study.

Figure 6B:
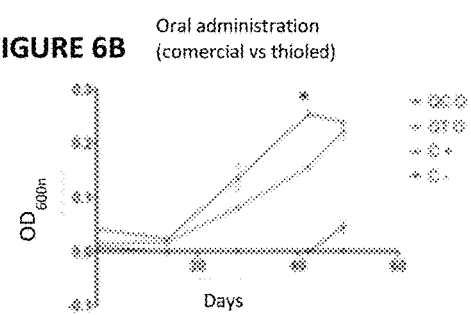
Figure 6:
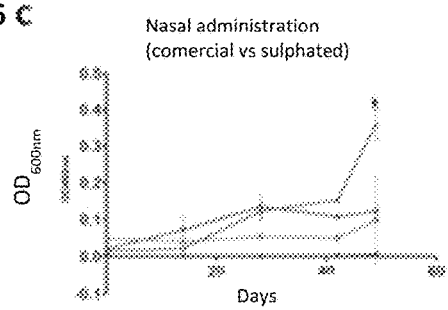
Figure 6D:
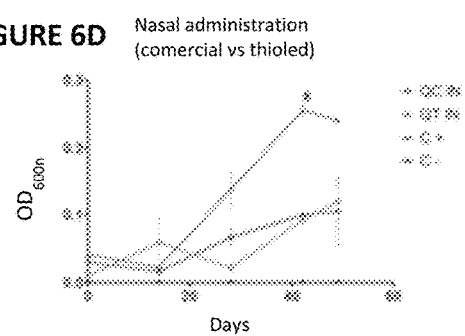
Figure 6:
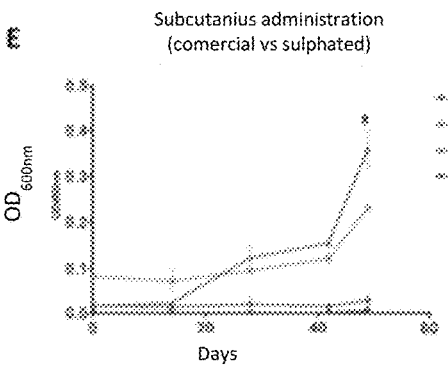
Figure 6F:
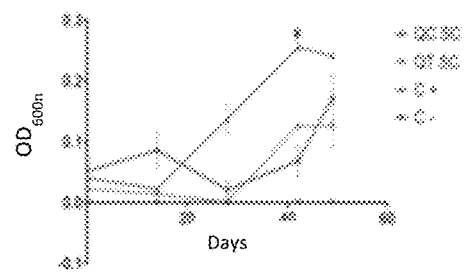
Figure 7A:
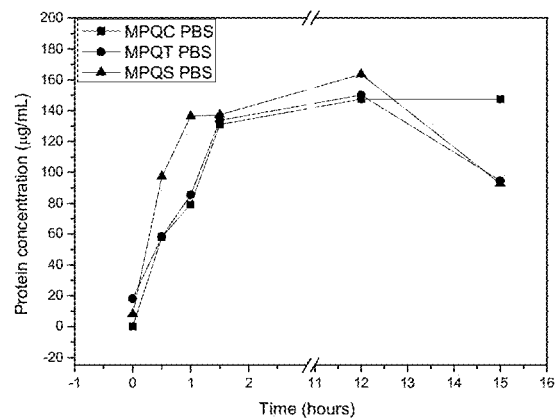
FIGS. 7A-7C illustrate a test protein release over time from microparticles made of commercial chitosan (MPQC), thiolated chitosan microparticles (MPQT), and sulfated chitosan microparticles (MPQs) in the presence of different solutions: PBS buffer (7A), simulated gastric fluid (7B) and simulated intestinal fluid (7C).
Figure 7B:
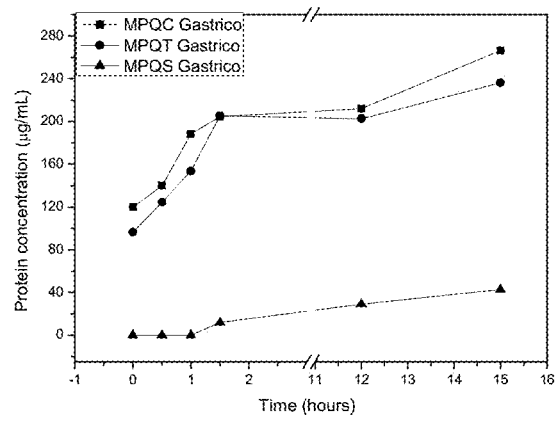
Figure 7C:
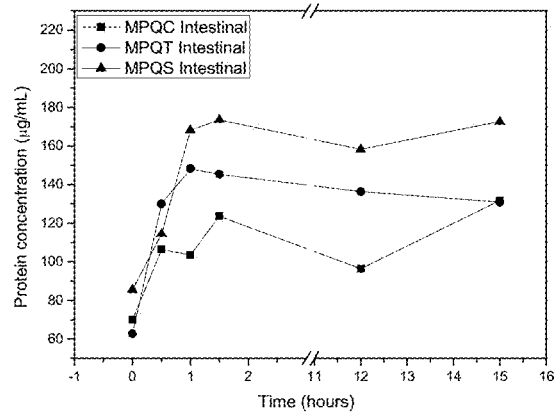
Figure 8A:
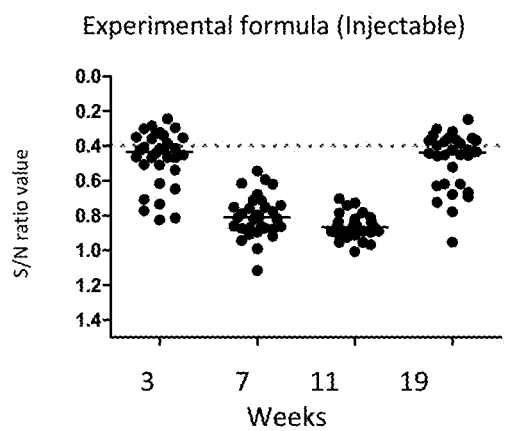
FIGS. 8A-8D illustrate Serological profiles of pigs immunized against PCV2 according treatment. S/N ratio≤0.4 is considered positive for the presence of antibodies in serum, while each sample showing an S/N ratio>0.4 is considered as negative. (A) Group 1 and 3. (B) Group 2 and 4. The dashed red line corresponds to the cutting off and black bar to the statistical average.
Figure 8B:
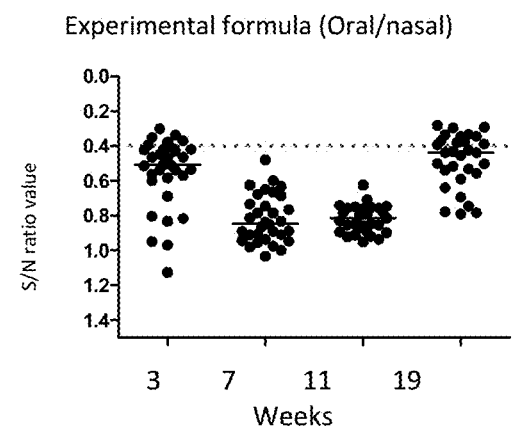
Figure 8C:
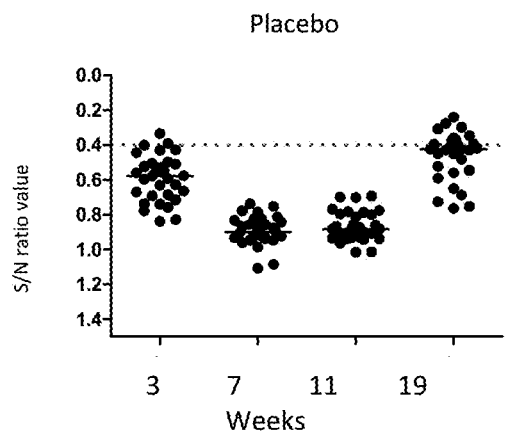
Figure 8D:
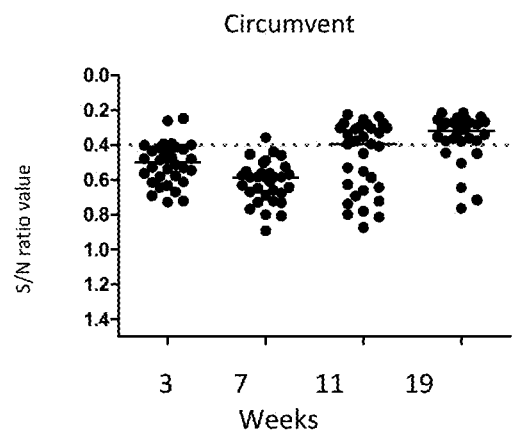

Under the data obtained in the study of in vitro protein release, the MPQC and MPQT being immersed in simulated gastric fluid without enzyme, presented early degradation (time zero) (see FIG. 6B). The acidic pH of simulated gastric fluid (pH=1.2) promote the breakdown of PMs, thereby permitting release of the encapsulated protein.

Instead the MPQs (FIG. 6B) protein released after 1 hour of experiment and considerably less, showing an effect of controlled release of antigen. Maximum release of protein for MPQC, MPQs and MPQT occurs at 15 hours.

Accordingly, and surprisingly the MPQs remain intact when immersed in simulated gastric fluid, meanwhile the microparticles MPQs submerged in simulated intestinal fluid having a controlled release of the protein encapsulated in time. Preliminary data from the study of in vitro release of proteins are substantial in the formulation of an oral vaccine, as to present an antigen release site directed ensures that PMs remain intact until the desired site of absorption (intestine) releasing the encapsulated antigenic protein and thus ensuring interaction of these two entities (microparticle and antigen) with M cells present in Peyer's patches of the intestinal epithelium. Thus, PMs would contact dendritic cells, promoting the development of an immune response. Moreover, in simulated intestinal fluid, the MPQC, MPQT MPQs and have a maximum average protein release at 1.5 hours after starting the study (see FIG. 6C). MPQs>MPQT>MPQC.

Consequently, MPQs microparticles offer better protection to the encapsulated antigen, when they are immersed in simulated gastric fluid as compared with MPQT MPQC and which exhibit degradation. This increases the bioavailability of the encapsulated agent since erosion is delayed sulphated particles, improving the stability of the agent to prevent its diffusion through the matrix and degradation or hydrolysis in an acidic medium, such as gastric.

In summary, the graphs show the presence of protein in time solutions that simulate the different compartments of the digestive system, information that allows us to infer the level of protection and the degree of release of antigen presenting MPs tested. For MPQC and MPQT very similar behavior in the gastric solution, corresponding to a rather lower than that given by MPQs (FIG. 6B) protection, demonstrating that MPQs retain their structural integrity in the gastric environment is observed.

In intestinal solution as release of antigen was achieved with MPQs, this result shows that not only is protected at the gastric level, but also its release is achieved intestine. Antigenic release was less in MPQT and the lowest was observed in MPQC.

It is important to consider that one of the major objectives in the pharmaceutical industry is to balance key factors affecting efficiency, "Protection"+"Liberation" in the therapeutic target. With this, the order of efficiency is MPQs>MPQT>MPQC.

Under these results obtained in an animal model, the technician typically versed in the area can extrapolate them to test any type of livestock, where the diseases are generated by infectious agents such as viruses, to Tables A, using sulfated polysaccharide macromolecules such as HS as cell receptor.

Example 15. Preclinical Trials in Pigs

The objective of this study was to determine the safety of experimental vaccine formulations against porcine circovirus type 2 (PCV-2) individuals administered in swine. For this the presence of reactions after immunization hypersensitivity was observed in addition to the visualization and palpation of the injection site for parenteral formulations, used as a parameter for these studies side effects reported in current commercial vaccines used in the market, which have the following adverse reactions post vaccination:

A transient rise in body temperature can occur until 2 days after vaccination.

Some piglets may be depressed and show a reduced feed intake for a few days.

A transient local reaction at the injection site can be observed.

It may be a hypersensitivity reaction; where animals could be recovered within minutes without any treatment.

In parallel, it was evaluated signology respiratory and/or digestive pigs immunized in both nasal/oral and injectable route.

Immunization was performed by administering vaccine formulations anti PCV-2 where microparticles (MPs) sulfated chitosan loaded Cap protein assembled as VLPs in yeast Saccharomyces cereviseae strain N30/pYES::orf2-optz (Bucarey et al., 2009) were used. These formulations were made from a solution of chitosan and sulphated recombinant yeast crude extract, using the technique of spray drying. The dose administered to each individual corresponded to 50 mg of PMs suspended in 2 mL PBS IX previously filtered and autoclaved ($\geq$12 µg antigen VLPs PCV-2 50 mg PMs each product or 2 mL). For this, the MPs were weighed on an analytical balance to complete 100 doses of vaccine, then dissolved in PBS 1×, such that the final formulation concentration was 2.5%. The complete formulation was bottled in high density polypropylene 250 mL designed for vaccine storage. Subsequently, the bottles were tightly sealed with aluminum seals and rubber stoppers following a standard commercial vaccine production.

Example 16. Experimental Design Trial in Pigs

The assay was performed in a unit of animal husbandry, in a pavilion rearing and fattening later one. The first corresponds to a flag commercial rearing, i.e., had the gold standard for growing pigs between 21 to 80 days of life. This pavilion allowed accommodation space 240 animals, feeding and sufficient for breeding of animals beberos. It also had control food intake, which calculates production parameters of pigs. As background, the site was positive for PCV-2 and other common infections in pigs, swine influenza, respiratory and reproductive syndrome pigs (PRRS), enzootic pneumonia (*Mycoplasma hyopneumoniae*), among others. The site was in a clean-up stage, so there is low stocking density, which implies that the animals are not exposed to a "natural" but much smaller, pathogen load resembling a controlled situation.

It is utilized 240 commercial pigs of both sexes, of 4 weeks of age, with a good body condition (CC), including 120 subjects were males and females were 120 were used. All individuals were divided into 8 groups of 30 pigs equivalents each, separated by sex, distributed in 8 pens of 12 m² solid floor each about.

Each animal was identified with one eartag color. plastic ear tags, which were placed in the right atrium of each pig using pincers for ear tags were used. They were used eartags red, yellow, white and green for identifying pigs according to the treatment and route of administration of the formulations.

All concerning the treatment of animals general procedure was performed by veterinarians in accordance with the provisions of the Guide for the Care and Use of Laboratory Animals by the Council for International Organizations of Biomedical Sciences. (Institute of Laboratory Animal Resources Commission on Life Sciences National Research Council, 1996).

Example 17. Immunization Under Semi-Controlled Conditions

Two vaccine formulations were used, called Formulation A and formulation B, and placebo formulation and the first commercial vaccine, administered in pigs at 4 weeks of age, followed by a booster at two weeks, oral/intranasal route and injection. Formulation A and formulation B are PMs suspended in 2 mL of PBS IX previously filtered and autoclaved (≥12 μg antigen VLPs of PCV-2). The placebo was PBS pH 7.4.

Immunization is performed according to the protocol described in Table 10, while the safety assessment of vaccine formulations against PCV-2 based crude extract yeast enriched VLPs PCV-2 microencapsulated sulfated chitosan (QS) was made at 7 days after each dose administered.

TABLE 10

Immunization schedule and safety assessment of pigs using vaccine formulations against PCV-2 based crude extract yeast enriched VLPs PCV-2 microencapsulated sulfated chitosan (QS).

| Age (Weeks) | Event |
|---|---|
| 1 | First dosis |
| 2 | First safe evaluation |
| 3 | Second dosis |
| 4 | Second safe evaluation |
| 22 | Sacrifice |

To determine the safety of the formulations used, the presence of reactions subsequent hypersensitivity to immunization, visualization and palpation of the injection site to sense if an inflammatory reaction in pigs were immunized parenterally, produced was evaluated in addition to the observation of respiratory and/or digestive signology in pigs immunized by the intranasal/oral and injectable route:

a) Hypersensitivity reaction: Corresponds.
b) Inflammatory reaction.
c) Respiratory signology,
d) Digestive signology.

Example 18. Hypersensitivity Assessment and Post-Vaccination Sinologias

No hypersensitivity reaction was observed in any of the pigs immunized with formulations A and B to receive the first and second dose. However, a pig received the first dose and two pigs receiving the second dose of the commercial formulation experienced a hypersensitivity reaction (Table 11), characterized by an increase in respiratory rate followed by a decompensation of the animal, with subsequent recomposition thanks to resuscitation by a veterinarian.

TABLE 11

Percentage of hypersensitivity reaction pigs immunized by the vaccine formulated using different routes of administration, compared with placebo and a commercial injectable vaccine.

| Group | No of animals | Treatment | Route of administration | $1^a$ dosis | $2^{nd}$ dosis |
|---|---|---|---|---|---|
| 1 | 30 | Form. A | Injectable | 0% (0) | 0% (0) |
| 2 | 30 | Form. A | Oral/intranasal | 0% (0) | 0% (0) |
| 3 | 30 | Form. B | Injectable | 0% (0) | 0% (0) |
| 4 | 30 | Form. B | Oral/intranasal | 0% (0) | 0% (0) |
| 5 | 30 | Placebo | Injectable | 0% (0) | 0% (0) |
| 6 | 30 | Placebo | Oral/intranasal | 0% (0) | 0% (0) |
| 7 | 30 | First commercial vaccine | Injectable | 3.3% (1) | 0% (0) |
| 8 | 30 | First commercial vaccine | Injectable | 0% (0) | 2% (6.6) |

No inflammatory reaction was observed in any of the pigs immunized with formulations A and B to receive the first and second dose. However, two pigs in Group 7 and one group 8 to the first dose of the commercial formulation had an inflammatory reaction at the injection site, and ten pigs in Group 7 and six pigs of group 8 to the second dose (table 12). This lesion is characterized by the increase in volume focused on the injection site, firm and with a variable number of small nodules. The volume increase varied between 2 and 7 cm in diameter. These lesions gradually disappeared over the course of days until complete resolution to approximately 15 days after vaccination.

TABLE 12

Percentage of pigs immunized inflammatory reaction using the vaccine formulated by different routes of administration, compared with placebo and a commercial injectable vaccine.

| Group | No of animals | Treatment | Route of administration | $1^{st}$ dosis | $2^{nd}$ dosis |
|---|---|---|---|---|---|
| 1 | 30 | Form. A | Injectable | 0% (0) | 0% (0) |
| 2 | 30 | Form. A | Oral/intranasal | 0% (0) | 0% (0) |
| 3 | 30 | Form. B | Injectable | 0% (0) | 0% (0) |
| 4 | 30 | Form. B | Oral/intranasal | 0% (0) | 0% (0) |
| 5 | 30 | Placebo | Injectable | 0% (0) | 0% (0) |
| 6 | 30 | Placebo | Oral/intranasal | 0% (0) | 0% (0) |

TABLE 12-continued

Percentage of pigs immunized inflammatory reaction using the vaccine formulated by different routes of administration, compared with placebo and a commercial injectable vaccine.

| Group | No of animals | Treatment | Route of administration | $1^{st}$ dosis | $2^{nd}$ dosis |
|---|---|---|---|---|---|
| 7 | 30 | First commercial vaccine | Injectable | 6.6% (2) | 33.3% (10) |
| 8 | 30 | First commercial vaccine | Injectable | 3.3% (1%) | 20% (6) |

Swine respiratory signology were observed during the course of the safety assessment of the first and second doses in all study groups (Table 13), characterized by paroxysmal cough. This can be explained due to campus health conditions in which it was carried out the study, not an alteration caused by the administered formulations.

TABLE 13

Percentage of respiratory signology immunized pigs using vaccine formulated by different routes of administration, compared with placebo and a commercial injectable vaccine.

| Group | No of animals | Treatment | Route of administration | $1^{st}$ dosis | $2^{nd}$ dosis |
|---|---|---|---|---|---|
| 1 | 30 | Form. A | Injectable | 10% (3) | 3.3% (1) |
| 2 | 30 | Form. A | Oral/intranasal | 20% (6) | 10% (3) |
| 3 | 30 | Form. B | Injectable | 23.3% (7) | 20% (6) |
| 4 | 30 | Form. B | Oral/intranasal | 26.6% (8) | 20% (6) |
| 5 | 30 | Placebo | Injectable | 23.3% (7) | 0% (0) |
| 6 | 30 | Placebo | Oral/intranasal | 16.6% (5) | 0% (0) |
| 7 | 30 | First commercial vaccine | Injectable | 13.3% (4) | 6.6% (2) |
| 8 | 30 | First commercial vaccine | Injectable | 16.6% (5) | 3.3% (1) |

Digestive signology pigs were observed during the course of the safety assessment of the first and second dose in all groups (Table 14), characterized by diarrhea. This can be explained due to campus health conditions in which it was carried out the study and/or food cause, and not to an alteration caused by the administered formulations.

TABLE 14

Percentage of digestive signology immunized pigs using vaccine formulated by different routes of administration, compared with placebo and a commercial injectable vaccine.

| Group | No of animals | Treatment | Route of administration | $1^{st}$ dosis | $2^{nd}$ dosis |
|---|---|---|---|---|---|
| 1 | 30 | Form. A | Injectable | 20% (6) | 0% (0) |
| 2 | 30 | Form. A | Oral/intranasal | 23.3% (7) | 0% (0) |
| 3 | 30 | Form. B | Injectable | 20% (6) | 0% (0) |
| 4 | 30 | Form. B | Oral/intranasal | 10% (3) | 6.6% (2) |
| 5 | 30 | Placebo | Injectable | 13.3% (4) | 0% (0) |
| 6 | 30 | Placebo | Oral/intranasal | 23.3% (7) | 0% (0) |
| 7 | 30 | First commercial vaccine | Injectable | 16.6% (5) | 0% (0) |
| 8 | 30 | First commercial vaccine | Injectable | 26.6% (8) | 0% (0) |

In conclusion, these results demonstrate that is safe to use by injection or oral/intranasal vaccine PCV-2 based crude extract yeast enriched VLPs PCV-2 microencapsulated sulfated chitosan (QS), therefore, the delivery oral/intranasal route can be an alternative strategy to efficiently induce anti-PCV antibody.

Example 19. Evaluation of Laboratory Parameters Post-Vaccination (Viral Load and Antibodies)

Blood samples were collected by puncture of the external jugular vein (3 mL approximately in tubes without anticoagulant, Vacutainer, Becton Dickinson and Company, USA)

with two weeks intervals in step rearing and every 3 weeks in the fattening stage. The samples were stored at refrigeration temperature and transported to the laboratory BIO-VETEC of the Faculty of Veterinary and Animal Sciences, University of Chile for processing. Each blood tube was centrifuged at 1800 rpm for 5 minutes to obtain the supernatant serum, which was aliquoted in sterile and free of nucleases 2 mL cryotubes subsequently labeled and stored at −80° C. until used for performing the technique ELISA, extraction of genetic material and real time PCR (qPCR).

Blood samples were collected by puncture of the external jugular vein (3 mL approximately in tubes without anticoagulant, Vacutainer, Becton Dickinson and Company, USA) with two week intervals in step rearing and every 3 weeks in the growing stage. Samples were stored at refrigeration temperature and transported to the laboratory for processing. Each blood tube was centrifuged at 1800 rpm for 5 minutes to obtain the supernatant serum, which was aliquoted in sterile and free of nucleases 2 mL cryotubes subsequently labeled and stored at −80° C. until used for performing the technique ELISA, extraction of genetic material and real time PCR (qPCR).

Assays for enzyme-linked immunosorbent (ELISA), PCV2 Ab Mono Blocking SERELISA (SYNBIOTICS, USA) commercial kit was used following the manufacturer's recommended protocol. Then we proceeded to reading in the microplate reader (Microplate reader Model 680, BIO-RAD) at a wavelength of 450 nm obtained by this measuring optical density of each sample. Finally, the value of each sample according to the formula shown below was calculated, where each sample showing an S/N ratio≤0.4 is considered positive for the presence of antibodies in serum, while each sample present an S/N ratio of >0.4 is considered as negative.

$$\text{S/N (Average OD absorbance reading of (2)=sample)/(average OD negative control)} \quad (2)$$

where OD is the optical density.

The GeneJET DNA Genomic Purification Kit (Thermo Scientific, Lithuania) commercial kit was used following the manufacturer's recommended protocol for DNA extraction. DNA extraction is complete, the product was stored at −20° C. until was analyzed by the technique of real time PCR (qPCR).

For performing qPCR technique, the following primers were used, which amplify a specific region PCV ORF2, sequences SEQ ID No:3 and SEQ ID No.: 4.

This technique was performed using a commercial kit called Kappa Sybr® Fast Universal qPCR Kit (Kapa Biosystems, USA) forming a masterbatch containing 4.2 µL nucleasar free water, 0.4 µL [10 µmol/µL], each specific partitioner, 10 µL 2× KAPA SYBR® FAST qPCR Master Universal Mix2, and 5 µL of temperate DNA, completing a final volume of 20 µL. Then we proceeded to amplify PCV2 ORF2 segment by the use of a thermal cycler (LightCycler® Nano, Roche). To amplify the genetic material of an initial denaturation at 95° C. for 3 minutes, then 40 cycles consisting of denaturation at 95° C. for 10 seconds and a phase alignment/extension is first carried out at 60° C. for 60 seconds. A dissociation curve was performed after amplification by gradually increasing the temperature of 60-95° C., and the fluorescence signal was measured every 0.1° C.

Absolute quantitation was performed by extrapolating from CT with those obtained in a dilution curve containing known concentrations of PCV2. To this a sample containing the plasmid into which is cloned the ORF1 gene of the virus and 2 was used. The plasmid DNA was extracted using the commercial kit AxyPrep™ Plasmid Miniprep Kit (Axygen Biosciences, USA) according to the manufacturer's instructions. The concentration of the control plasmid preparation was determined by EPOCH Bio Tek spectrophotometer. Thus, they were used in the reactions of the standard amplification curve serial dilutions (1/100,000 to 1/1,000,000,000) concentrations (ng/µL) of plasmid DNA in known nuclease-free water.

For the implementation of this technique, pooles 4 serum samples each were performed, for a total of 32 reactions sample; as to the amplification of temperate only in duplicate was done for the DNA standards. The samples used for this analysis correspond to weeks 3, 11 and 19.

As for the statistical analysis, the ANOVA test was used to determine if significant differences exist between the eight treatment groups as to the difference in the results of antibody levels. Initially tested independently for each of the weeks (7, 11, 13 and 19) ANOVA was performed. To compare the difference of ELISA values between groups using the integrated results of every week, a mixed linear model was made considering the variable ELISA (S/N value) as the dependent variable, the variables weeks (weeks of 7, 11 and 19) and the variable group as fixed effects, and identification (ID) of each pig as random factor, which takes into account that there is independence of the measured data in the same individual.

With respect to the viral load, the results were tabulated by number of positive pools per group per week. Furthermore, these data were graphed as PCV2 values Log copies/ml serum in each of the groups according to treatment. Statistical tests were not performed because the number of positive samples obtained were limited and not presenting a parametric behavior, as seen in the table and graph above. The results are discussed below. FIGS. 8A-8D shows that antibodies are present in all groups against PCV2 at 3 weeks, corresponding to maternal antibodies, which tend to decrease in all groups at 7 weeks of age, showing a similar behavior those observed in field studies where maternal antibodies begin to decrease from infancy to the rearing period (Blanchard et al 2003; Caraova et al 2007; Grau-Roma et al 2009; Larochelle et al 2003). It was observed that the decrease of the antibody titers at 7 weeks of age in the experimental groups (injectable and oral/intranasal) and commercial significantly different from placebo (p<0.05). This would be explained by the beginning of a rising antibody titer induced by both experimental formulations as that commercial, attenuating thus lowering the display maternal antibodies.

Moreover, it was observed that in week 11 there are no significant differences between groups, oral/intranasal and placebo injectable experimental formulation, however, the group vaccinated with the commercial formulation mark significant differences from the previous (p<0.05). Finally, at week 19 it was marked up appreciated antibody titer in all groups and no significant difference between them (p<0.05).

Regarding the viral load in Table 15 and FIGS. 9A-9D shows, by qPCR, all groups at 3 weeks of age are positive to PCV2 in at least one of the pools except the injectable formulation experimental group. However, all groups were positive at week 11 with a median log 8 copies of DNA/mL. Finally, at week 19 only injectable formulation experimental group achieving viral load down to zero in all samples.

TABLE 15

Number of positive pools per group by qPCR technique.

| Group | Week 3 | Week 11 | Week 19 |
|---|---|---|---|
| Injectable formulation | 0/8 | 8/8 | 0/8 |
| Oral/intranasal formulation | 1/8 | 8/8 | 5/8 |
| Placebo | 3/8 | 5/8 | 3/8 |
| First commercial vaccine | 4/8 | 7/8 | 1/8 |

Importantly, all positive samples showed a viral load that ranged between 6.29 and 9.39 log copies of DNA/mL serum, therefore, the viral load found in these pools during the period of this study suggests that positive pigs exhibited moderate to severe PCV2 infection, as has been reported to exceed 105.3 copies of DNA/mL serum would be compatible with an infection that could impact productivity animals gain values, such as daily weight (Lopez-Soria et al., 2014).

The dynamics of antibodies against PCV2 viral load and during the swine production observed in this test for both control and experimental groups did not differ from serological dynamics observed in other production campuses Chile active vaccination programs. However, there is a difference of load viral, which although has the same trend presents viral loads much higher, which can be explained by the active presence of PRRS virus on campus, so that due to high load this pathogen, the site is in a closing process, possibly entail to a poor health condition of the pigs.

As mortality observed both at the stage of rearing as feedlot, this was higher than expected in a commercial establishment, as in step rearing mortality was 2.91% and the growing stage was 4.27%, as shown in Table 16. remarkably, in the only groups mortalities were observed, corresponding to two of (oral/intranasal and injectable) experimental groups. This increased mortality can be explained by the active presence of PRRSV circulating on campus. Based on the macroscopic lesions observed at necropsy, they are mainly related to conditions associated pneumonic *Haemophilus parasuis* and *Streptococcus suis*, which concomitan bacteria infected by PCV2.

TABLE 16

Table of mortality during the study animals presented.

| | Group 1 | Group 2 | Group 3 | Group 4 | Group 5 | Group 6 | Group 7 | Group 8 |
|---|---|---|---|---|---|---|---|---|
| Post-weaning | 0/30 | 0/30 | 0/30 | 1/30 | 1/30 | 1/30 | 1/30 | 3/30 |
| Finishing | 0/30 | 0/30 | 4/30 | 1/29 | 3/29 | 0/29 | 1/29 | 1/27 |

In conclusion, it was possible to estimate the efficacy of the experimental vaccine by analyzing the antibody titer and viral load of PCV2 immunized pigs used in this trial.

Example 20. Evaluation of the Production Parameters in Baby Pigs Post-Vaccination The purpose of this example was to evaluate the effectiveness of experimental vaccine formulations against porcine circovirus type 2 (PCV-2) administered in individual swine, by analysis of production data obtained in this study, corresponding to the gain daily (GDP) and feed efficiency (ECA).

Pigs weighing was performed at 3, 13 and 21 weeks of age using a model platform Condor, indicator XK3119-P LCD RS-232 (1600 kg×200 gr 1.20×1.20 mt) and a cage to keep animals in the proper position for correct weighing.

To estimate whether there are significant differences in productivity between different treatment groups, the difference in weight was measured (in each pig) between week 13 and week 3 and the weight difference between week 19 and week 13. The average of these differences in weight per group was calculated. To estimate whether the differences are statistically significant between groups, ANOVA test was performed.

The results are set forth below. In Table 17 the obtained data are presented in productive stage recria shows that by analyzing the feed conversion efficiency for group differences accumulated between them, ranging from 1.81 to 2.00, the lowest observed in group 3 (Injectable experimental) and 8 (commercial vaccine) and the highest in groups 1 (injectable experimental) and 4 (Experimental oral/intranasal).

TABLE 17

Production parameters per group during the post-weaning period.

| | Weeks | $\overline{X}$ of weight per week (kg) | $\overline{X}$ ADG per pig (kg)[1] | $\overline{X}$ CTAC per group (kg)[2] | $\overline{X}$ CTAC per pig (kg)[3] | ECAA per group[4] | $\overline{X}$ ADGA per pig (gr)[5] |
|---|---|---|---|---|---|---|---|
| Group 1 | 3 | 9.39 | 33.42 | 2010 | 67 | 2.00 | 419 |
| | 13 | 42.81 | | | | | |
| Group 2 | 3 | 9.33 | 35.24 | 2050 | 68.33 | 1.94 | 518 |
| | 13 | 44.57 | | | | | |
| Group 3 | 3 | 7.67 | 32.22 | 1750 | 58.33 | 1.81 | 474 |
| | 13 | 39.89 | | | | | |
| Group 4 | 3 | 7.41 | 33.53 | 1948.40 | 67.19 | 2.00 | 493 |
| | 13 | 40.94 | | | | | |
| Group 5 | 3 | 7.18 | 33.41 | 1875.01 | 64.66 | 1.94 | 491 |
| | 13 | 40.59 | | | | | |
| Group 6 | 3 | 7.08 | 35.01 | 1887.40 | 65.08 | 1.86 | 515 |
| | 13 | 42.09 | | | | | |
| Group 7 | 3 | 6.81 | 33.05 | 1811.47 | 62.46 | 1.89 | 486 |
| | 13 | 39.86 | | | | | |

TABLE 17-continued

Production parameters per group during the post-weaning period.

| | Weeks | $\overline{X}$ of weight per week (kg) | $\overline{X}$ ADG per pig (kg)[1] | $\overline{X}$ CTAC per group (kg)[2] | $\overline{X}$ CTAC per pig (kg)[3] | ECAA per group[4] | $\overline{X}$ ADGA per pig (gr)[5] |
|---|---|---|---|---|---|---|---|
| Group 8 | 3 | 6.27 | 30.96 | 1546.27 | 57.27 | 1.85 | 455 |
| | 13 | 37.23 | | | | | |

[1]Average total weight gain per pig in each group.
[2]Total amount of food consumed per group.
[3]Average total amount of food consumed by pigs in each group.
[4]Cumulative feed conversion efficiency per group.
[5]Average daily weight gain per pig accumulated in each group.

The analysis of average daily weight gain accruing revealed no significant differences between groups (Table 21).

In Table 18 the production data from the fattening pigs are presented. Here, it is noted that by analyzing the efficiency of partial feed conversion per group there are significant differences between them, observing the lowest in groups 4 (oral/intranasal experimental) and 8 (commercial vaccine) and higher in the groups 5 (placebo) and 7 (commercial vaccine).

The analysis of the average gain partial daily weight per group shows that there are significant differences between them, specifically between groups 1 (injectable experimental) and 4 (oral/intranasal experimental), groups 1 and 6 (placebo) and between groups 1 and 7 (commercial vaccine) (Table 22 and 23).

In the table N 19 evidenced significant differences between the groups to analyze the efficiency of feed conversion accumulated during the period of this study, being the most efficient Group 6 (placebo) and Group 7 (commercial vaccine) less efficient.

TABLE 18

Production parameters per group during the fattening period.

| | Weeks | $\overline{X}$ of weight per week (kg) | $\overline{X}$ ADG per pig (kg)[1] | CTAC per group (kg)[2] | $\overline{X}$ CTAC per pig (kg)[3] | ECAA per group[4] | $\overline{X}$ ADGA per pig (gr)[5] |
|---|---|---|---|---|---|---|---|
| Group 1 | 13 | 42.81 | 58.66 | 5080 | 169.33 | 2.89 | 1011 |
| | 21 | 101.46 | | | | | |
| Group 2 | 13 | 44.57 | 53.81 | 4680 | 156.00 | 2.90 | 928 |
| | 21 | 98.38 | | | | | |
| Group 3 | 13 | 39.89 | 58.25 | 4402.84 | 169.34 | 2.91 | 1004 |
| | 21 | 98.15 | | | | | |
| Group 4 | 13 | 40.94 | 51.21 | 4117.35 | 147.05 | 2.87 | 883 |
| | 21 | 92.15 | | | | | |
| Group 5 | 13 | 40.59 | 54.01 | 4240.42 | 163.09 | 3.02 | 931 |
| | 21 | 94.60 | | | | | |
| Group 6 | 13 | 42.09 | 50.10 | 4300.00 | 148.28 | 2.96 | 864 |
| | 21 | 92.19 | | | | | |
| Group 7 | 13 | 39.86 | 53.53 | 4740.00 | 169.29 | 3.16 | 923 |
| | 21 | 93.39 | | | | | |
| Group 8 | 13 | 37.23 | 51.34 | 3820.00 | 146.92 | 2.86 | 885 |
| | 21 | 88.57 | | | | | |

[1]Average total weight gain per pig in each group.
[2]Total amount of food consumed per group.
[3]Average total amount of food consumed by pigs in each group.
[4]Cumulative feed conversion efficiency per group.
[5]Average daily weight gain per pig accumulated in each group.

Based on the analysis of cumulative daily gain weight, it is observed that there are significant differences between groups, specifically between groups 1 and 4, 1 and 6 and between groups 1 and 8.

TABLE 19

Production parameters per group during the study period.

| | Group 1 | Group 2 | Group 3 | Group 4 | Group 5 | Group 6 | Group 7 | Group 8 |
|---|---|---|---|---|---|---|---|---|
| ECAA[1] | 2.56 | 2.51 | 2.51 | 2.52 | 2.60 | 2.50 | 2.67 | 2.48 |
| GPDA[2] | 730 | 706 | 718 | 672 | 693 | 675 | 687 | 653 |

[1]Average feed conversion efficiency accumulated
[2]Average daily weight gain accumulated The general behavior of the data obtained in this study can be explained by the active presence of PRRSV on campus, characterized by loss of appetite, depression, lethargy, fever (Christopher-Hennings et al., 1995b) and pneumonia, thus causing a decrease in growth rate in post-weaning pigs (Rosso et al., 1994; Dee et al., 1997).

The average weight differences between week 3 and 13 and between 11 weeks and 19 below in the following table.

TABLE 20

Average weight difference between week 3, 13 and 19 per group.

| Group | Average weight difference between week 11-3 | Average weight difference between week 19-11 |
|---|---|---|
| 1 | 33.42 | 58.66 |
| 2 | 35.24 | 53.81 |
| 3 | 32.22 | 56.74 |
| 4 | 33.53 | 51.38 |
| 5 | 33.39 | 52.50 |
| 6 | 34.99 | 50.10 |
| 7 | 33.05 | 52.76 |
| 8 | 30.90 | 50.65 |

According to the ANOVA test, no significant differences ($p<0.05$) between groups for difference weeks 13 and 3 (Table 21), but if there are significant differences between groups for the measured weight between weeks 13 and 19 (Table 22), as shown below.

TABLE 21

ANOVA weight differences between pigs week 3 and week 13.

| | Digrees of freedom | Sum of squares | Half quadratic | F | Pr (>F) |
|---|---|---|---|---|---|
| Group | 7 | 389 | 55.54 | 1.181 | 0.315 |
| Residual | 225 | 10582 | 47.03 | | |

TABLE 22

ANOVA weight differences by group of pigs between week 13 week 19.

| | Digrees of freedom | Sum of squares | Half quadratic | F | Pr (>F) |
|---|---|---|---|---|---|
| Group | 7 | 1782 | 254.59 | 3.587 | 0.00113 |
| Residual | 215 | 15262 | 70.99 | | |

In conclusion, the efficacy of the experimental vaccine was estimated by the analysis of production data obtained in this study, corresponding to the daily weight gain (GDP) and feed conversion efficiency accumulated (ECA).

Analysis of the cumulative feed conversion efficiency during the rearing period showed significant differences between groups, ranging from 1.81 to 2.00, and analysis of feed conversion efficiency obtained during the course of the study showed that also significant differences between groups, ranging from 2.48 to 2.67, showing a difference of 3.5% between experimental groups and placebo.

They based on the cumulative daily gain no significant differences between the groups in step rearing were observed, but a significant difference at the end of fattening period were apparent, varying from 653-730 grams. Differences were observed between groups 1 (injectable experimental) and 6 (placebo) and between groups 1 and 7 (commercial vaccine), the group 1 which received the highest daily gain, showing a difference of 7.6% compared to placebo.

The general behavior of the data obtained in this example can be explained by the active presence of PRRSV on campus, causing a decrease in the growth rate in post-weaning pigs.

Example 21. Sulfated Chitosan Concentration Effect Over the PCV2 Capsid Protein The improvement of the microencapsulated antigen that use heparan sulfate as a cellular receptor would differ from previous research that already include the microparticles formulation with sulfated chitosan. The following results reinforce the effect that a specific binding of the sulfated chitosan has over PCV2 virus title, where it was evident at a specific concentration of the sulfated biopolymer (chitosan).

According to FIG. 10, the trial shows that a 2% sulfated biopolymer (chitosan) concentration would be the ideal to bond a viral antigen (PCV2 capsid protein). Furthermore, the qPCR graph in FIG. 10 shows an effect of the sulfated chitosan concentration in the bond with the PCV2 virus, where the viral title gets smaller while the percentage of sulfated chitosan increases.

Example 22. Sulfated Chitosan Molecular Weight Effect Over the PCV2 Capsid Protein The effect that a specific binding of the sulfated chitosan has over PCV2 virus title was evident in a specific type of chitosan with a lower molecular weight. This shows that previous research could not address the effect over the process where microencapsulated antigen could bond naturally to heparan sulfate as a celluar receptor.

The trial of FIG. 11 shows that the lower molecular weight (<75 kDa) biopolymer (chitosan) has a higher effect over the viral title (PCV2) when compared to a higher molecular weight counterpart. Moreover, the qPCR graph in FIG. 11 shows an effect over the PCV2 viral title that depends on what type of sulfated chitosan was used. The greater effect was with the sulfated chitosan with a lower molecular weight (<75 kDa) in relation with sulfated chitosan with higher molecular weights.

Example 23. Sulfated Chitosan and Non-Sulfated Chitosan Effect Over the PCV2 Capsid Protein The generation of a new immunogenic formulation that presents a surprising effect in the bonds of certain antigens reinforce the non-obviousness of the invention especially when the sulfated chitosan groups could bond efficiently to the specific PCV2 antigens versus the non-sulfated chitosan groups.

It was evaluated the effect of sulfated-versus non-sulfated-biopolymer (chitosan) over a viral title (PCV2), were the latter would not be bond efficiently to the antigen (PCV2 capsid protein). The qPCR graph in FIG. 12 shows an effect over the PCV2 viral title that depends on the presence of sulfate groups. Non-sulfated chitosan would not be bond efficiently with PCV2 antigen. In contrast, the sulfated version low their viral title more efficiently than the commercial chitosan by itself.

---

The invention claimed is:

1. Immunogenic formulation for veterinary use, comprising:

a viral antigen whose cellular receptor is heparan sulfate;

a low molecular weight (LMW) biopolymer with units of D-glucosamine and N-acetyl-D-glucosamine functionalized with thiolated or sulfated groups at 1% to 2%, wherein the antigen is microencapsulated by said biopolymer, and the formulation is for oral, intranasal or parenteral administration.

2. The immunogenic formulation of claim 1, wherein said biopolymer is selected from chitosan and chitin.

3. The immunogenic formulation of claim 1, wherein the biopolymer has a degree of deacetylation greater than 50%.

4. The immunogenic formulation of claim 1, wherein the antigen is obtained from Porcine Circovirus type 2 (PCV2), Porcine Reproductive and Respiratory Syndrome Virus (PRRSV), Classical swine fever (PPC), porcine epidemic diarrhea (PED), virus transmissible gastroenteritis swine virus, swine vesicular disease (SVD), vesicular stomatitis virus (VSV) or African swine fever virus (ASFV).

5. The immunogenic formulation of claim 4, wherein said antigen is the PCV2 capsid protein.

6. The immunogenic formulation of claim 5, wherein the PCV2 capsid protein comprises the SEQ. ID. NO. 2 sequence.

7. The immunogenic formulation of claim 1, wherein said formulation comprises 6 to 25 μg of antigen per mL.

8. The immunogenic formulation of claim 1, wherein said microparticles have a size of 1 to 20 μm and a zeta potential value of −30 to +30 mV.

9. The immunogenic formulation of claim 1, wherein said formulation is administered to an animal for the prevention and prophylaxis of diseases associated to heparan sulfate (HS) as cell receptor.

10. The immunogenic formulation of claim 9, wherein said animal is swine.

* * * * *